US009763821B2

(12) United States Patent
Romo

(10) Patent No.: US 9,763,821 B2
(45) Date of Patent: Sep. 19, 2017

(54) ORTHOPEDIC DEVICE FOR DYNAMICALLY TREATING THE KNEE

(71) Applicant: Ossur Iceland ehf, Reykjavik (IS)

(72) Inventor: Harry Duane Romo, Aliso Viejo, CA (US)

(73) Assignee: Ossur Iceland ehf, Reykjavik (IS)

( * ) Notice: Subject to any disclaimer, the term of this patent is extended or adjusted under 35 U.S.C. 154(b) by 0 days.

(21) Appl. No.: 15/016,631

(22) Filed: Feb. 5, 2016

(65) Prior Publication Data

US 2016/0151188 A1 Jun. 2, 2016

Related U.S. Application Data

(63) Continuation-in-part of application No. 14/839,133, filed on Aug. 28, 2015, which is a continuation of application No. 13/664,824, filed on Oct. 31, 2012, now Pat. No. 9,125,730.

(60) Provisional application No. 61/553,341, filed on Oct. 31, 2011.

(51) Int. Cl.
*A61F 5/00* (2006.01)
*A61F 5/01* (2006.01)

(52) U.S. Cl.
CPC .... *A61F 5/0123* (2013.01); *A61F 2005/0134* (2013.01); *A61F 2005/0137* (2013.01); *A61F 2005/0172* (2013.01); *A61F 2220/0008* (2013.01); *A61F 2250/001* (2013.01)

(58) Field of Classification Search
None
See application file for complete search history.

(56) References Cited

U.S. PATENT DOCUMENTS

| D73,768 S | 1/1868 | Allen |
| 1,601,659 A | 9/1926 | Van Harlingen |
| 2,195,024 A | 3/1940 | Bullock |
| 2,467,907 A | 4/1949 | Peckham |

(Continued)

FOREIGN PATENT DOCUMENTS

| DE | 33 20 274 A1 | 12/1984 |
| DE | 196 31 632 A1 | 2/1998 |

(Continued)

OTHER PUBLICATIONS

Defrate, Louis E., et al., "In Vivo Function of the Posterior Cruciate Ligament During Weightbearing Knee Flexion", The American Journal of Sports Medicine, Dec. 2004, pp. 1923-1928, vol. 32, No. 8, Publisher: American Orthopaedic Society for Sports Medicine, Published by SAGE; http://ajs.sagepub.com/content/32/8/1923.

(Continued)

*Primary Examiner* — Kim M Lewis
(74) *Attorney, Agent, or Firm* — Workman Nydegger

(57) ABSTRACT

An orthopedic device includes a hinge assembly, a frame having first and second frame components spaced apart from and connected to one another by the hinge assembly, a strap system extending between medial and lateral sides of the first frame component, and at least one tensioning element. The at least one tensioning element has a first end secured to the strap system and a second end coupled to the hinge assembly. Articulation of the hinge assembly pulls the strap system toward the frontal plane by the at least one tensioning element.

20 Claims, 15 Drawing Sheets

(56) References Cited

U.S. PATENT DOCUMENTS

| | | | |
|---|---|---|---|
| 2,536,454 A | 1/1951 | McIntyre |
| 2,558,986 A | 7/1951 | Seelert |
| 2,959,168 A | 11/1960 | Shook |
| 3,444,560 A | 5/1969 | Northup, Jr. |
| 3,753,625 A | 8/1973 | Fabrizio et al. |
| 3,976,057 A | 8/1976 | Barclay |
| 4,064,569 A | 12/1977 | Campbell |
| 4,088,130 A | 5/1978 | Applegate |
| 4,100,918 A | 7/1978 | Glancy |
| 4,145,766 A | 3/1979 | May |
| 4,220,148 A | 9/1980 | Lehneis |
| 4,298,992 A | 11/1981 | Burstein et al. |
| 4,320,747 A | 3/1982 | Daniell, Jr. |
| 4,340,041 A | 7/1982 | Frank |
| 4,361,142 A | 11/1982 | Lewis et al. |
| 4,370,977 A | 2/1983 | Mauldin et al. |
| 4,372,298 A | 2/1983 | Lerman |
| 4,397,308 A | 8/1983 | Hepburn |
| 4,407,276 A | 10/1983 | Bledsoe |
| 4,428,369 A | 1/1984 | Peckham et al. |
| 4,433,679 A | 2/1984 | Mauldin et al. |
| 4,463,751 A | 8/1984 | Bledsoe |
| 4,489,718 A | 12/1984 | Martin |
| 4,506,661 A | 3/1985 | Foster |
| 4,508,111 A | 4/1985 | Hepburn |
| 4,520,802 A | 6/1985 | Mercer et al. |
| 4,523,585 A | 6/1985 | Lamb et al. |
| 4,649,906 A | 3/1987 | Spademan |
| 4,655,201 A | 4/1987 | Pirmantgen |
| 4,657,000 A | 4/1987 | Hepburn |
| 4,691,694 A | 9/1987 | Boyd et al. |
| 4,697,583 A | 10/1987 | Mason et al. |
| 4,723,539 A | 2/1988 | Townsend |
| 4,732,143 A | 3/1988 | Kausek et al. |
| 4,733,656 A | 3/1988 | Marquette |
| 4,768,762 A | 9/1988 | Lund |
| 4,773,404 A | 9/1988 | Townsend |
| 4,790,299 A | 12/1988 | Marquette |
| 4,793,333 A | 12/1988 | Marquette |
| 4,817,588 A | 4/1989 | Bledsoe |
| 4,856,500 A | 8/1989 | Spademan |
| 4,856,501 A | 8/1989 | Castillo et al. |
| 4,865,024 A | 9/1989 | Hensley et al. |
| 4,890,607 A | 1/1990 | Townsend |
| 4,911,709 A | 3/1990 | Marlow et al. |
| 4,955,369 A | 9/1990 | Bledsoe et al. |
| 4,961,416 A | 10/1990 | Moore et al. |
| 4,966,133 A | 10/1990 | Kausek |
| 4,982,732 A | 1/1991 | Morris |
| 4,991,571 A | 2/1991 | Kausek |
| 5,002,045 A * | 3/1991 | Spademan ............ A61F 5/0125 602/16 |
| 5,018,514 A | 5/1991 | Grood et al. |
| 5,020,797 A | 6/1991 | Burns |
| 5,038,765 A | 8/1991 | Young et al. |
| 5,052,375 A | 10/1991 | Stark et al. |
| 5,063,917 A | 11/1991 | Young et al. |
| 5,176,622 A | 1/1993 | Anderson et al. |
| 5,213,094 A | 5/1993 | Bonutti |
| 5,230,696 A | 7/1993 | Silver et al. |
| 5,230,697 A | 7/1993 | Castillo et al. |
| 5,261,871 A | 11/1993 | Greenfield |
| 5,347,894 A | 9/1994 | Fischer |
| 5,357,654 A | 10/1994 | Hsing-Chi |
| 5,437,611 A | 8/1995 | Stern |
| 5,443,444 A | 8/1995 | Pruyssers |
| 5,456,268 A | 10/1995 | Bonutti |
| 5,472,410 A | 12/1995 | Hamersly |
| 5,472,412 A | 12/1995 | Knoth |
| 5,514,082 A | 5/1996 | Smith, III |
| 5,575,764 A | 11/1996 | Van Dyne |
| 5,588,956 A | 12/1996 | Billotti |
| 5,599,288 A | 2/1997 | Shirley et al. |
| 5,624,390 A | 4/1997 | Van Dyne |
| 5,628,722 A | 5/1997 | Solomonow et al. |
| 5,658,241 A | 8/1997 | Deharde et al. |
| 5,662,596 A | 9/1997 | Young |
| 5,683,353 A | 11/1997 | Hamersly |
| 5,685,830 A | 11/1997 | Bonutti |
| 5,807,294 A | 9/1998 | Cawley et al. |
| 5,827,208 A | 10/1998 | Mason et al. |
| 5,857,988 A | 1/1999 | Shirley |
| 5,873,847 A | 2/1999 | Bennett et al. |
| 5,891,061 A | 4/1999 | Kaiser |
| 5,891,071 A | 4/1999 | Stearns et al. |
| 5,921,946 A | 7/1999 | Tillinghast et al. |
| 5,950,245 A | 9/1999 | Binduga |
| 5,954,677 A | 9/1999 | Albrecht et al. |
| 5,997,493 A | 12/1999 | Young |
| 6,001,075 A | 12/1999 | Clemens et al. |
| 6,004,283 A | 12/1999 | Young |
| 6,074,355 A | 6/2000 | Bartlett |
| 6,110,137 A | 8/2000 | Bastyr et al. |
| 6,129,690 A | 10/2000 | Hamlin et al. |
| RE37,209 E | 6/2001 | Hensley et al. |
| 6,245,034 B1 | 6/2001 | Bennett et al. |
| RE37,297 E | 7/2001 | Smith, III |
| 6,290,664 B1 | 9/2001 | Nauert |
| 6,331,169 B1 | 12/2001 | Bastyr et al. |
| 6,409,693 B1 | 6/2002 | Brannigan |
| 6,413,232 B1 | 7/2002 | Townsend et al. |
| 6,425,166 B1 | 7/2002 | Seligman et al. |
| 6,436,058 B1 | 8/2002 | Krahner et al. |
| 6,471,664 B1 | 10/2002 | Campbell et al. |
| 6,500,138 B1 | 12/2002 | Irby et al. |
| 6,551,264 B1 | 4/2003 | Cawley et al. |
| 6,666,837 B2 | 12/2003 | Weihermuller |
| 6,740,054 B2 | 5/2004 | Stearns |
| 6,752,775 B2 | 6/2004 | Seligman et al. |
| 6,834,752 B2 | 12/2004 | Irby et al. |
| 6,875,187 B2 | 4/2005 | Castillo |
| 6,936,020 B2 | 8/2005 | Davis |
| 6,993,808 B1 | 2/2006 | Bennett et al. |
| 7,004,919 B2 | 2/2006 | Gaylord et al. |
| 7,037,287 B2 | 5/2006 | Cormier et al. |
| 7,059,329 B2 | 6/2006 | Mason et al. |
| 7,074,201 B2 | 7/2006 | Reinecke et al. |
| 7,097,627 B2 | 8/2006 | Enzerink et al. |
| 7,117,569 B2 | 10/2006 | Bledsoe |
| 7,150,721 B2 | 12/2006 | Houser |
| 7,182,740 B1 | 2/2007 | Castillo |
| 7,192,407 B2 | 3/2007 | Seligman et al. |
| 7,198,610 B2 | 4/2007 | Ingimundarson et al. |
| 7,201,728 B2 | 4/2007 | Sterling |
| 7,207,960 B2 | 4/2007 | Kenney |
| 7,235,058 B2 | 6/2007 | Doty et al. |
| 7,235,059 B2 | 6/2007 | Mason et al. |
| 7,309,322 B2 | 12/2007 | Albrecht et al. |
| 7,311,687 B2 | 12/2007 | Hoffmeier et al. |
| D577,828 S | 9/2008 | Ingimundarson et al. |
| 7,431,708 B2 | 10/2008 | Sreeramagiri |
| 7,435,234 B2 | 10/2008 | Gamada |
| 7,485,103 B2 | 2/2009 | Mason et al. |
| 7,500,957 B2 | 3/2009 | Bledsoe |
| 7,534,217 B2 | 5/2009 | Seligman et al. |
| 7,534,219 B2 | 5/2009 | Stearns |
| 7,544,174 B2 | 6/2009 | Nathanson |
| 7,553,289 B2 | 6/2009 | Cadichon |
| 7,597,675 B2 | 10/2009 | Ingimundarson et al. |
| 7,662,122 B2 | 2/2010 | Sterling |
| 7,722,555 B2 | 5/2010 | Doty et al. |
| 7,727,174 B2 | 6/2010 | Chang et al. |
| 7,749,183 B2 | 7/2010 | Ingimundarson et al. |
| 7,757,303 B2 | 7/2010 | Miller |
| 7,806,842 B2 | 10/2010 | Stevenson et al. |
| 7,811,242 B2 | 10/2010 | Seligman |
| 7,846,115 B2 | 12/2010 | Seligman et al. |
| 7,850,632 B2 | 12/2010 | Gilmour |
| 7,927,299 B2 | 4/2011 | Krause |
| 7,963,933 B2 | 6/2011 | Nace |
| 8,048,013 B2 | 11/2011 | Ingimundarson et al. |
| 8,128,587 B2 | 3/2012 | Stevenson et al. |
| 8,376,974 B2 | 2/2013 | Nace |
| 8,882,688 B1 | 11/2014 | Ancinec |

(56) References Cited

U.S. PATENT DOCUMENTS

| | | | |
|---|---|---|---|
| 8,920,350 B2 | 12/2014 | Merkley et al. | |
| 2002/0013544 A1 | 1/2002 | Stearns | |
| 2002/0052568 A1 | 5/2002 | Houser et al. | |
| 2002/0133108 A1 | 9/2002 | Jagodzinski | |
| 2004/0002674 A1 | 1/2004 | Sterling | |
| 2004/0049140 A1 | 3/2004 | Doty et al. | |
| 2004/0054307 A1 | 3/2004 | Mason et al. | |
| 2004/0054311 A1 | 3/2004 | Sterling | |
| 2004/0068215 A1 | 4/2004 | Adelson et al. | |
| 2004/0097859 A1 | 5/2004 | Stearns | |
| 2005/0015156 A1 | 1/2005 | Hikichi | |
| 2005/0020951 A1 | 1/2005 | Gaylord et al. | |
| 2005/0177082 A1 | 8/2005 | Bledsoe | |
| 2005/0245853 A1 | 11/2005 | Scorvo | |
| 2005/0273025 A1 | 12/2005 | Houser | |
| 2006/0100560 A1 | 5/2006 | Gilmour | |
| 2006/0100561 A1 | 5/2006 | Gilmour | |
| 2006/0116616 A1 | 6/2006 | Albrecht et al. | |
| 2006/0135902 A1 | 6/2006 | Ingimundarson et al. | |
| 2006/0142680 A1 | 6/2006 | Iarocci | |
| 2007/0010772 A1 | 1/2007 | Ryan | |
| 2007/0100265 A1 | 5/2007 | Gamada | |
| 2007/0232972 A1 | 10/2007 | Martinez | |
| 2007/0270976 A1 | 11/2007 | DeHarde et al. | |
| 2008/0051684 A1 | 2/2008 | Gamada | |
| 2008/0066272 A1 | 3/2008 | Hammerslag et al. | |
| 2008/0195013 A1 | 8/2008 | Ingimundarson et al. | |
| 2008/0200856 A1* | 8/2008 | Cadichon | A61F 5/0123 602/32 |
| 2008/0249448 A1 | 10/2008 | Stevenson et al. | |
| 2008/0294079 A1 | 11/2008 | Sterling et al. | |
| 2009/0054819 A1 | 2/2009 | Einarsson | |
| 2009/0076426 A1 | 3/2009 | Einarsson et al. | |
| 2009/0099495 A1 | 4/2009 | Campos et al. | |
| 2009/0099562 A1 | 4/2009 | Ingimundarson et al. | |
| 2009/0105622 A1 | 4/2009 | Sterling et al. | |
| 2009/0124948 A1 | 5/2009 | Ingimundarson et al. | |
| 2009/0171469 A1 | 7/2009 | Thorsteinsson et al. | |
| 2009/0240181 A1 | 9/2009 | Sreeramagiri et al. | |
| 2009/0259154 A1 | 10/2009 | Nace | |
| 2009/0287128 A1 | 11/2009 | Ingimundarson et al. | |
| 2010/0010409 A1 | 1/2010 | Bejarano | |
| 2010/0056970 A1 | 3/2010 | Nace | |
| 2010/0162539 A1 | 7/2010 | Rancon | |
| 2011/0098618 A1 | 4/2011 | Fleming | |
| 2012/0046585 A1 | 2/2012 | Lee et al. | |
| 2012/0059296 A1 | 3/2012 | Kompa | |
| 2012/0157902 A1 | 6/2012 | Castillo et al. | |
| 2013/0110020 A1 | 5/2013 | Ingimundarson et al. | |
| 2013/0150761 A1 | 6/2013 | Romo et al. | |
| 2013/0172797 A1* | 7/2013 | Merkley | A61F 5/0102 602/16 |
| 2013/0178771 A1 | 7/2013 | Moir et al. | |
| 2013/0331754 A1 | 12/2013 | Dunn et al. | |
| 2014/0213948 A1 | 7/2014 | Romo et al. | |
| 2015/0005685 A1 | 1/2015 | Chetlapalli et al. | |

FOREIGN PATENT DOCUMENTS

| | | |
|---|---|---|
| DE | 196 45 076 A1 | 5/1998 |
| DE | 198 11 925 A1 | 10/1999 |
| DE | 10 259 751 A1 | 7/2004 |
| DE | 10 2010 006 089 A1 | 8/2010 |
| EP | 0 841 044 A1 | 5/1998 |
| EP | 0 941 722 A1 | 9/1999 |
| EP | 1 114 619 A1 | 7/2001 |
| EP | 1 302 184 A1 | 4/2003 |
| EP | 1 575 464 A1 | 9/2005 |
| EP | 1 880 802 A2 | 1/2008 |
| EP | 2 612 624 A1 | 7/2013 |
| FR | 2 122 846 A5 | 9/1972 |
| FR | 2 486 852 A1 | 1/1982 |
| FR | 2 663 380 A1 | 12/1991 |
| FR | 2 723 842 A1 | 3/1996 |
| FR | 2 777 489 A1 | 10/1999 |
| FR | 2 828 093 A1 | 2/2003 |
| GB | 1 213 855 A | 11/1970 |
| NO | 2009126724 A2 | 10/2009 |
| WO | 86/04228 A1 | 7/1986 |
| WO | 95/27451 A1 | 10/1995 |
| WO | 96/16615 A1 | 6/1996 |
| WO | 2004/056293 A1 | 7/2004 |
| WO | 2006/044423 A2 | 4/2006 |
| WO | 2010/087899 A2 | 8/2010 |

OTHER PUBLICATIONS

Cascade, "Jack PCL Brace", Oct. 2004, Publisher: Cascade Orthopedic Supply, Inc., Published in: US. http://www.cascade-usa.com/customer/caorsu/images/PDF/SSN_jackPCL.pdf downloaded, 1 page.

Markolf, Keith L., et al., "Changes in Knee Laxity and Ligament Force After Sectioning the Posteromedial Bundle of the Posterior Cruciate Ligament", Arthroscopy: The Journal of Arthroscopic and Related Surgery, Oct. 2006, pp. 1100-1106, vol. 22, No. 10, Publisher: Arthroscopy Association of North America, Published in: US.

Papannagari, Ramprasand, et al., "Function of Posterior Cruciate Ligament Bundles During In Vivo Knee Flexion", The American Journal of Sports Medicine, Sep. 2007, pp. 1507-1512, vol. 35, No. 9, Publisher: American Orthopaedic Society for Sports Medicine, Published by SAGE; http://ajs.sage.pub.com/content/35/9/1507.

Bledsoe Axiom/Axiom-D Custom & OTS Knee Brace, "Application Instructions & Patient Manual: Instructions for ACL or PCL Symptoms", Jan. 2007, pp. 1-4, vol. CP020223, Rev B, Publisher: Bledsoe Brace Systems, Published in: US. http://www.bledsoebrace.com/pdf/AI/Axiom-AI.pdf.

Brochure: Armor Fourcepoint, Donjoy Product pages http://www.donjoy.com/armorfp. Downloaded, Oct. 2011, 2 pages. Published: US.

Brochure: "Fusion OA", Breg 360 Customer Care, Product page http://www.breg.com/knee-bracing/oa/fusion-oa.html, downloaded, Oct. 2011, 2 pages. Publisher: Orthofix, Published in: US.

Brochure: "Fusion XT OA", Bregg 360 Customer Care, Product page http://www.breg.com/knee-bracing/oa/fusion-xt-oa.html, downloaded, Oct. 2011, 2 pages. Publisher: Orthofix, Published in: US.

Brochure: "CTI Custom", Ossur Product page from http://www.ossur.com/?PageID=13230 downloaded, Oct. 2011, 2 pages. Publisher: Ossur Americas, Published in: US.

Brochure: "X2K-OA", Bregg 360 Customer Care, Product page http://www.breg.com/knee-bracing/oa/x2k-oa.html. Downloaded, Oct. 2011, 1 page. Publisher: Orthofix, Published in: US.

International Search Report and Written Opinion regarding Application No. PCT/US2011/051627, Jan. 6, 2012.

International Search Report from corresponding PCT Application No. PCT/US2012/062702, Feb. 15, 2013.

International Preliminary Report on Patentability regarding Application No. PCT/US2011/051627, Mar. 28, 2013.

Menetrey, Jacques, "PCL: Conservative Treatment", 4th Advanced Course on Knee Surgery, Jan. 22-27, 2012. http://www.kneecourse.com/download/seminar_2012/monday/MENETREY%20Conservative%20treatment.pdf, 37 pages.

Extended European Search Report from EP Application No. 12150517.6, May 22, 2012.

Smith, Sean D. et al., "Functional bracing of ACL injuries: current state and future directions", Knee Surgery Sports Traumatology Arthhroscopy, Springer, Apr. 27, 2013, 11 pages.

Knapik, Joseph J. et al., Isometric, Isotonic and Isokinetic Torque Variations in Four Muscle Groups Through a Range of Joint Motion, "Physical Therapy: Journal of the American Physical Therapy Association and de Fysiotherapeut", 1983, vol. 63, No. 6, pp. 938-947, downloaded from http://ptjournal.apta.org/ on Apr. 15, 2014.

International Search Report and Written Opinion from International Application No. PCT/US2014/013245, May 6, 2014.

(56) References Cited

OTHER PUBLICATIONS

Jansson, Kyle S. et al., "A Historical Perspective of PCL Bracing", Knee Surgery Sports Traumatology Arthhroscopy, Springer-Verlag, May 24, 2012, 7 pages.
International Search Report from corresponding International Application No. PCT/US2014/042989, Oct. 15, 2014.

* cited by examiner

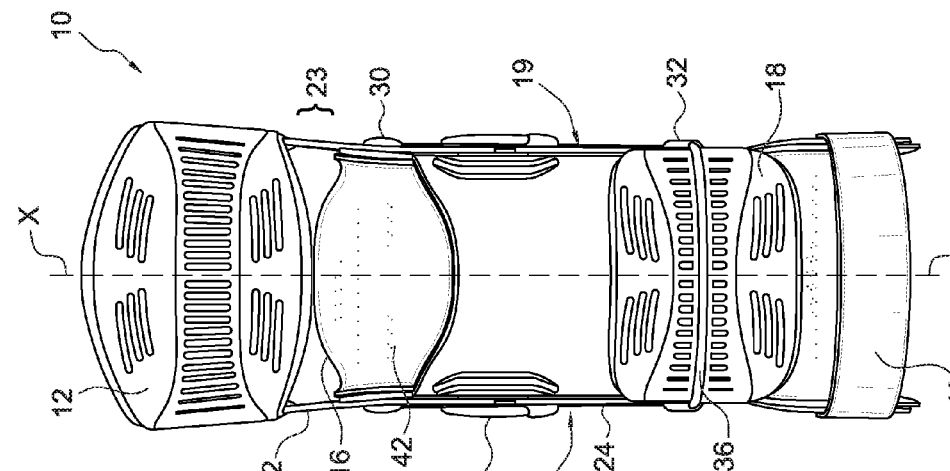
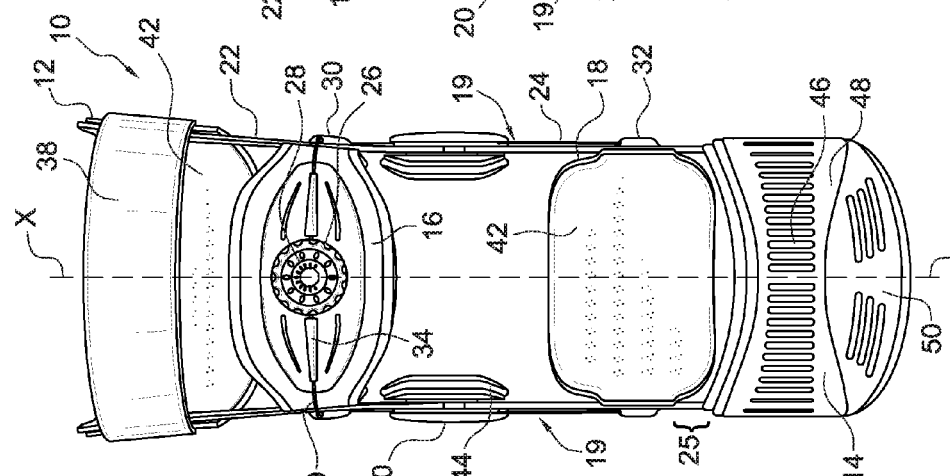
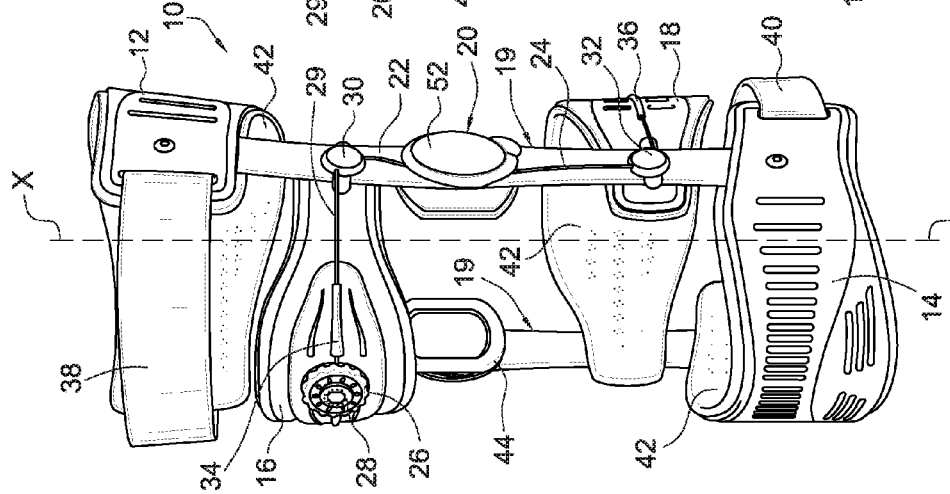

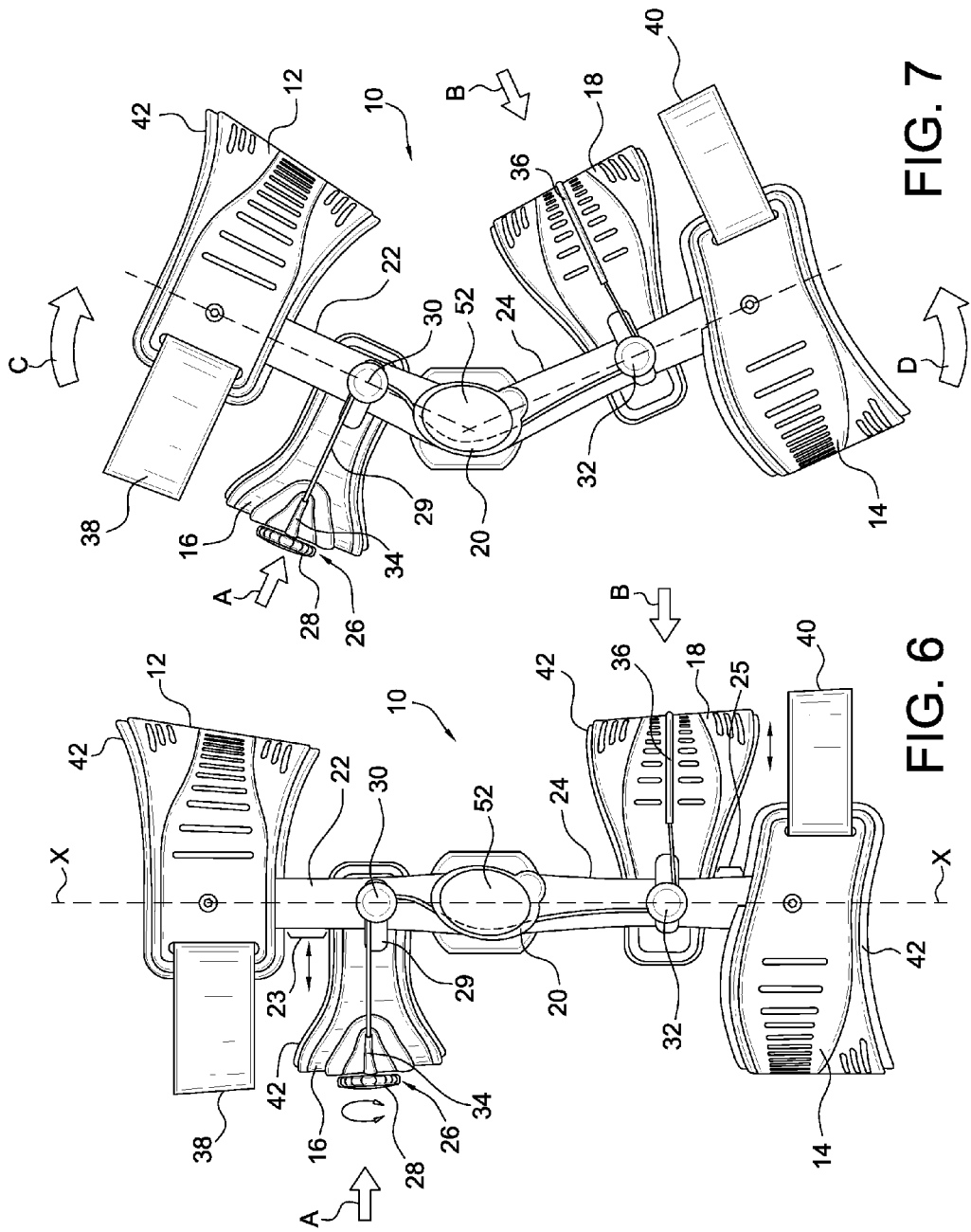

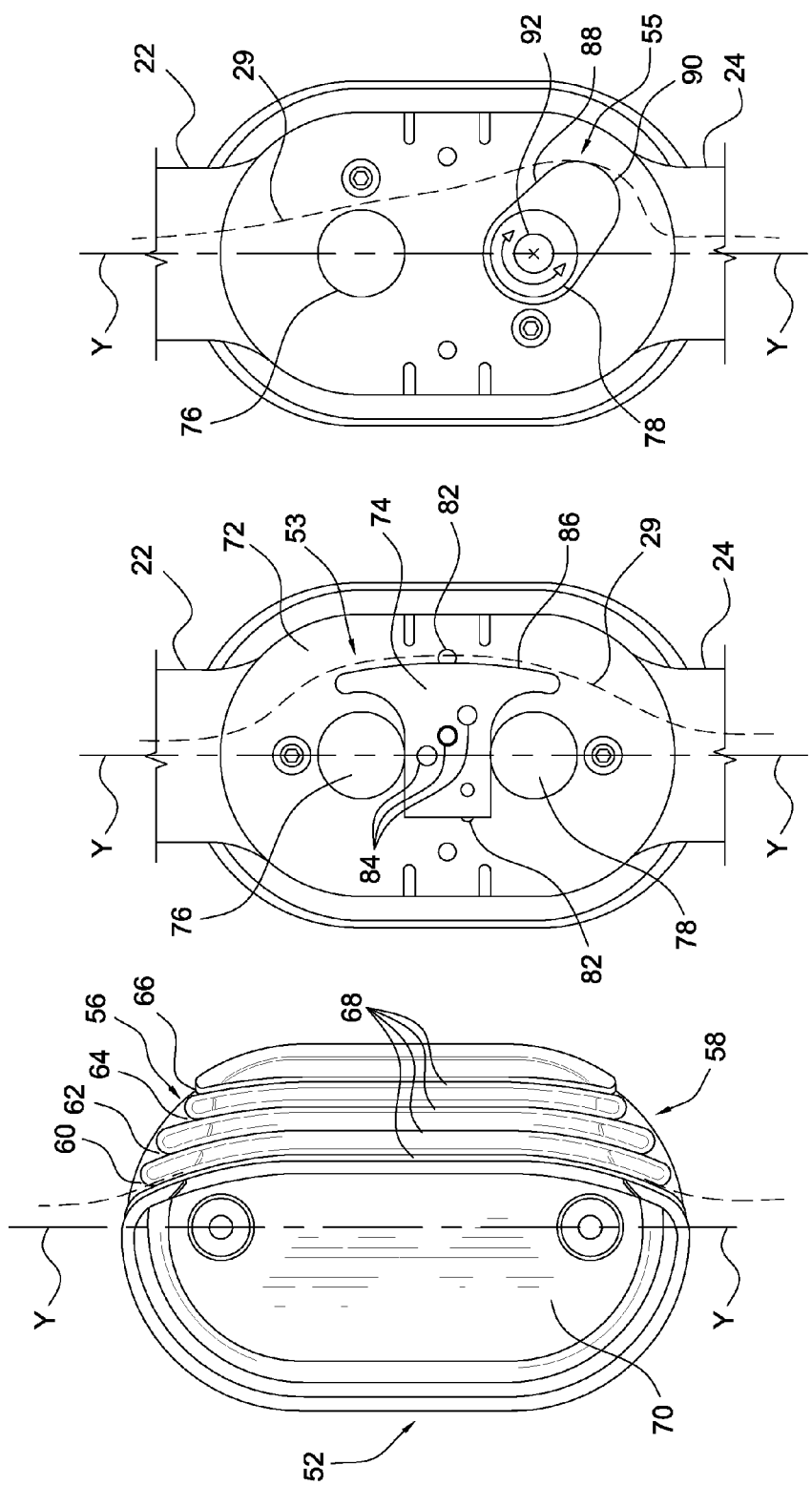

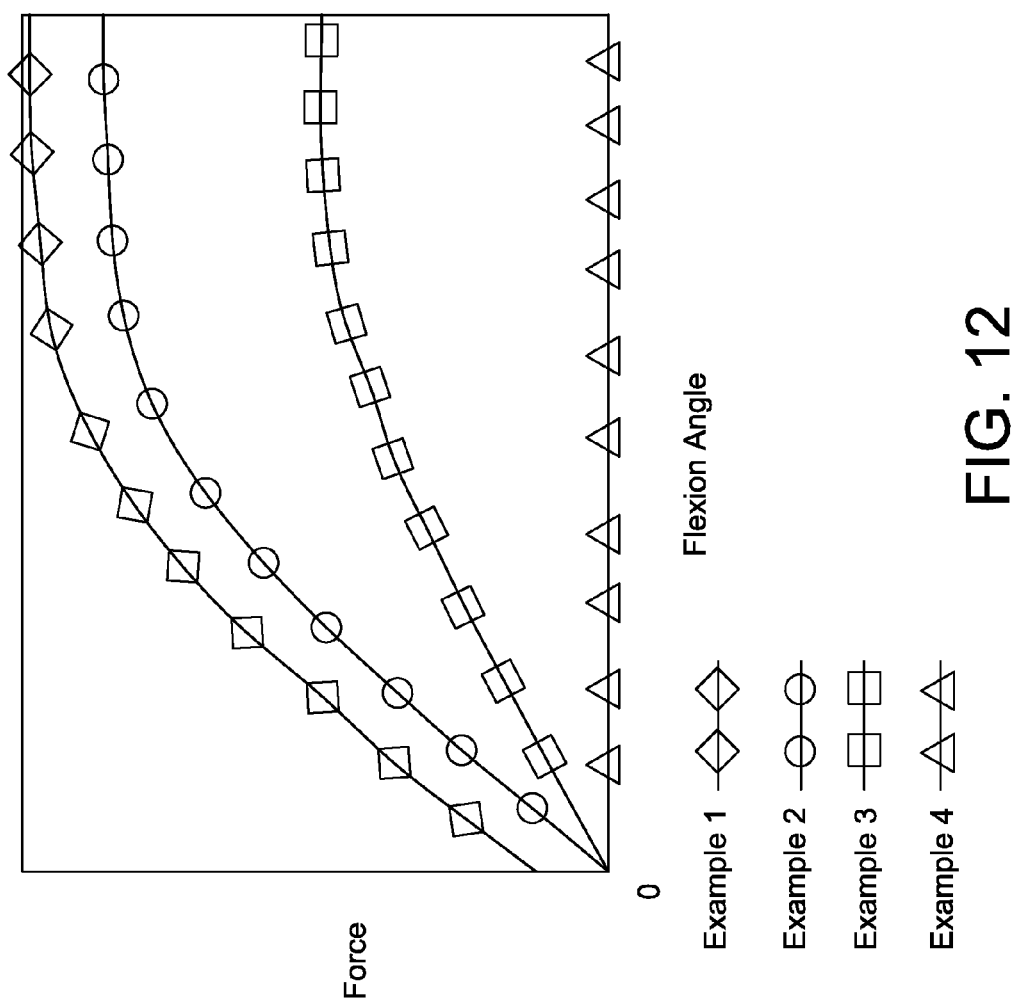

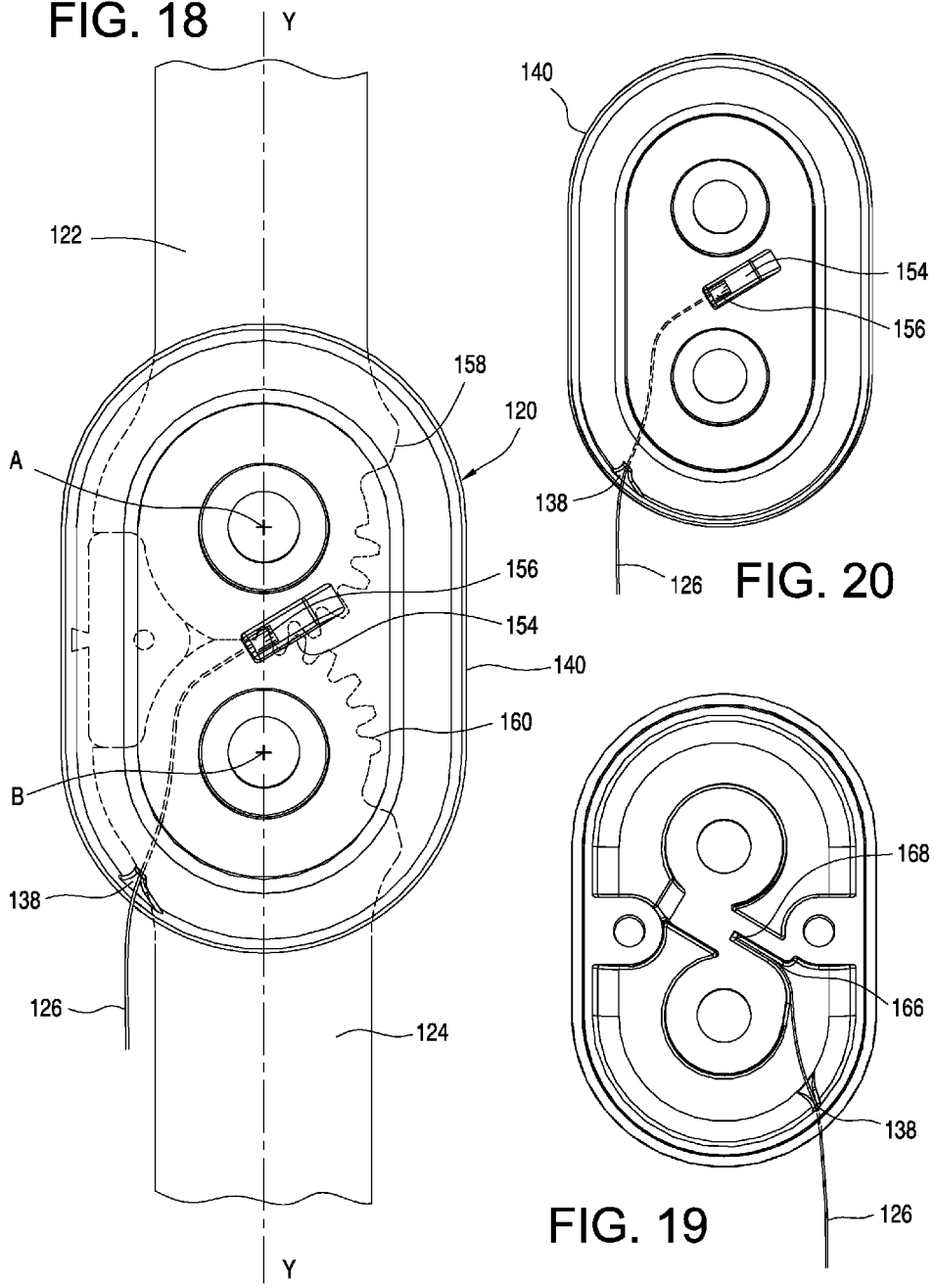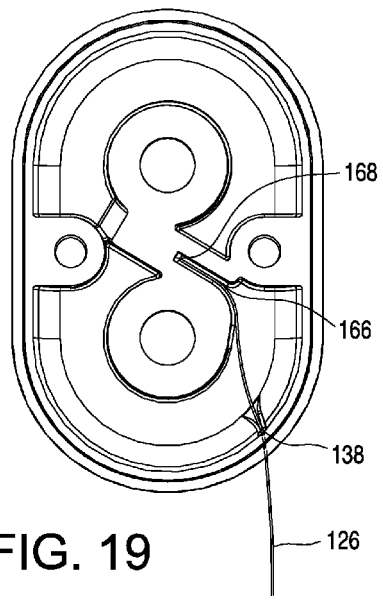

ORTHOPEDIC DEVICE FOR DYNAMICALLY TREATING THE KNEE

CROSS-REFERENCE TO RELATED APPLICATIONS

The application is a continuation of U.S. application Ser. No. 14/839,133, filed on Aug. 28, 2015, which is a continuation of U.S. application Ser. No. 13/664,824, filed on Oct. 31, 2012, now U.S. Pat. No. 9,125,730, issued on Sep. 8, 2015, which claims the benefit of U.S. provisional application No. 61/553,341, filed on Oct. 31, 2011.

FIELD OF THE DISCLOSURE

The disclosure relates to an orthopedic device, and more particularly to an orthopedic device for dynamically treating or supporting injuries of the knee.

BACKGROUND

Stabilization of the knee joint (femur and tibia) is understood to be created primarily by four key ligaments: the anterior cruciate ligament (ACL), the posterior cruciate ligament (PCL), the medial collateral ligament (MCL) and the lateral collateral (LCL) ligament. The ACL is much better known, in part because injuries to the ACL are much more commonly diagnosed. The ACL keeps the tibia from sliding too far forward (anterior) with respect to the femur. Conversely, as depicted in FIG. 1, the PCL prevents the tibia from sliding too far backwards (posterior) with respect to the femur.

PCL tears are graded by severity (I, II or III) of the injury. The grade is classified by the degree of increased posterior tibia translation compared with that of the contralateral knee. In general, grading of the injury corresponds to the following:

Grade 1: The ligament is mildly damaged and has been slightly stretched, but is still able to help keep the knee joint stable. 1-5 mm.

Grade 2: The ligament stretches to the point where it becomes loose. This is often referred to as a partial tear of the ligament. 6-10 mm Grade 3: This type of injury is most commonly referred to as a complete tear of the ligament. The ligament has been torn into two pieces, and the knee joint is unstable. 10 mm and greater.

As illustrated in FIG. 2, a PCL injury is typically sustained in a fall where the tibia is forced posteriorly regarding the femur. Another common way this injury occurs is when the knee hits the dash in a motor vehicle accident. PCL deficient knees may include significant knee pain and arthrosis in the medial and patellofemoral compartments. While the exact mechanism of articular degeneration in PCL-deficient knees is unknown, it has been found that PCL deficiency leads to significant increases of contact pressure in the medial and patellofemoral compartments, possibly leading to an increase in compartmental pressure due to increased anterior-posterior laxity and rotational instability of the knee.

PCL knee injuries often go surgically untreated, and a common form of treatment is to permit the PCL to heal on its own. When a PCL is torn, the proximal end of the tibia has a tendency to shift posteriorly which causes strain on the healing PCL, and results in a healed PCL longer than it was prior to injury. The healed knee may experience slack wherein the proximal end of the tibia shifts posteriorly after healing, causing a feeling of instability in the patient, and increasing the risk for further injury.

PCL injuries often are not isolated, and it has been found that concomitant posterolateral corner (PLC) injuries are common, particularly in a trauma setting. The PLC resists excessive varus and external rotation forces in the knee, and the PLC has a secondary role in resisting posterior translation of the tibia. When an injury of the PLC is combined with an injury of the PCL, the primary and secondary restraining effects of a tight PCL are lost at high knee-flexion angles. The PLC and PCL play a symbiotic role in resisting excessive external rotation and posterior translation of the proximal tibia.

The natural history of chronic PLC injuries includes varus thrust gait, posterolateral instability, and developing arthrosis. Similar to PCL-deficient knees, developing arthrosis in PLC-deficient knees is likely due to altered knee kinematics and increased peek compartment pressures.

An orthopedic device, such as a knee brace that provides support to the back of the upper calf throughout the range of motion, may be used to prevent this unwanted shifting. In the post-operative patient (or even the recently injured patient, who has not had, or will have, surgery), this may mitigate the lengthening of the PCL during healing, and prevent the shifting problems described above. In the patient having a PCL that has healed in a lengthened state, the brace may prevent the undesirable shifting described above, giving the patient an added feeling of stability, and a decreasing risk of further injury.

Unfortunately due to poor diagnostic methods, there is uncertainty as to the annual volume of PCL tears (estimated between 3% and 20% of all ligament injuries). PCL injuries have historically been considered to have benign clinical consequence. Thus if the PCL tear had been diagnosed, it would often go untreated since it resides outside the joint capsule and has the ability to heal itself. Unfortunately, when left to heal on its own, the PCL typically heals in an elongated length, resulting in joint instability.

Recent estimates place the number of diagnosed PCL tears in the US near 25,000 annually. When compared to the number of ACL tears, it places the percentage at roughly 10%. The question still remains as to how many knees go undiagnosed. The problem is that if an effort is not made to repair the ligament to maintain its normal length, it will heal in a stretched position, creating excessive movement between femoral and tibial joint surfaces; this raises the likelihood of degenerative changes in the knee leading to osteoarthritis.

PCL reconstruction has been recommended by some clinicians for more severe injuries, or for PCL injuries combined with other types of injuries. Even though some in-vitro biomechanical studies have reported that PCL reconstruction can restore knee biomechanics in a model with an isolated injury, the actual surgical management of PCL injuries has been problematic; a high number of patients continue to experience residual knee laxity after surgery.

Loads on the PCL have been shown to be dynamic in nature. As the knee is moved for instance, from a position of full extension to 90° of flexion, the tension on the normal intact PCL ligament increases. This increased tension helps to keep the tibia properly positioned with respect to the femur. When the PCL is damaged, it is not able to provide this increased tension and may allow the tibia to shift posteriorly. As mentioned above, if a brace could apply an external force to the posterior calf and in proper measure, it would provide the forces necessary to effectively co-locate the femur and tibia. It has been found that one possible cause for poor patient outcomes in treatment of the acute PCL injury is that the dynamic loads pull the tibia posteriorly during the healing process, and cause the PCL to heal in an elongated length. This may also result in an increased incidence of future osteoarthritis.

A properly designed dynamic brace could prevent or mitigate this occurrence. If surgery is required, this brace could offer protection for the reconstructed PCL throughout its healing process. Since the PCL is extracapsular and has the ability to heal on its own, such a brace may potentially prevent the need for surgical management. For the patient who has had a previous PCL injury and experiences joint laxity as no subsequent surgical intervention was undertaken, this brace may also provide enhanced stability and confidence. Ultimately, such an orthopedic device could benefit patients with all levels of PCL injuries. Another cause of poor outcomes is due to the gravity effect. As the patient lays supine and lifts the leg with the knee extended, the tibia falls posteriorly. This effect can be a regular occurrence while the patient is in the non weight bearing post operative phase where they can regularly experience this posterior shifting of the tibia simply by laying in bed.

The posterior shift of the tibia can be detrimental to the healing PCL and cause undue tension leading to a non-anatomical lengthening of the ligament. There are many PCL brace options available, however the known solutions lack certain critical functional requirements. Most options are static braces that only provide a constant anterior force through the entire arc of knee motion. While these static braces are capable of providing some stability to PCL-deficient knees, they do not adjust the stability in high degrees of knee flexion. Tension within the PCL varies through the knee arc motion.

Therefore, it is proposed herein to provide an orthopedic device in an exemplary form of a PCL brace that meets the certain critical functional requirements to effectively treat a PCL injury of the knee, and concomitant other injuries of the knee such as the PLC and patellofemoral pain. The proposed device will be to help support the functional healing of an acute PCL injury post operatively or non-operatively. Another purpose is to maintain the proper bone alignment of the femur and tibia for the patient with poorly healed/elongated PCL. Thus, the proposed device would be appropriate for all new PCL injuries and all those patients who never received surgery to preserve PCL length.

SUMMARY

In accordance with various orthopedic device embodiments described herein, an exemplary dynamic brace may be used in at least the following scenarios: (1) protection of the PCL post operatively during the healing process (3-6 months), such that once the PCL has been confirmed to be properly healed, the brace would be no longer needed unless the patient desires a brace for additional stability during activity; (2) protection of the PCL non-operatively whereby the brace provides dynamic stability allowing the PCL to heal under proper tension without surgery; (3) protection of the PCL for those individuals whose PCL has healed in an elongated position, whereby the brace provides dynamic stability of the PCL for activities; (4) reducing patellofemoral compartment pressures in PCL- and combined PCL/PLC-deficient knees, particularly at high degrees of knee flexion.

In accordance with an embodiment of the dynamic device or brace, unlike in static braces, a dynamic device is a knee brace arranged for dynamically treating a knee to provide increased anterior force and improved posterior stability at higher degrees of knee flexion to better mimic the natural activity of the PCL and/or the PLC. By improving the knee kinematics by a dynamic brace, the medial and patellofemoral compartment pressures in PCL- or PCL/PLC or other deficient knees can be normalized and possibly reduce the incidence of knee arthrosis.

The brace has a central axis and a frontal plane parallel to and intersecting the central axis and dividing the brace along first and second sides. The brace has a medial-lateral plane dividing the device into medial and lateral sides, which are generally oriented perpendicular to the frontal plane. The brace includes a hinge assembly, a frame having an upper cuff and a lower cuff spaced apart from and connected by the hinge assembly. A dynamic calf shell is connected to the frame and extends along the first side of the brace.

An adjustment system is connected to the dynamic calf shell and includes a tensioning element operatively engaging the dynamic calf shell and the hinge assembly. The dynamic calf shell is drawn anteriorly, creating an anteriorly directed force on the proximal tibia in the sagittal plane as the orthopedic device goes from an extension orientation to a flexion orientation. It has been found from this orientation that as the tensioning element shortens when the knee flexes, there is a generation of increased calf loads that in turn urges the tibia anteriorly to compensate for an impaired PCL.

The brace further comprises a strut segment connecting the lower cuff to the hinge assembly, and the tensioning element extends along at least part of the strut segment, preferably along the second side. In the case of arranging the brace for treating an impaired PCL, the tensioning element extends along the anterior side of the strut segment. The dynamic calf shell is secured to the strut segment and the tensioning element extends along at least part of the dynamic calf shell, with the dynamic calf shell being located on the distal posterior side of the brace when configured for treating the PCL.

In accordance with an embodiment, the tensioning element has a first end anchored to the hinge assembly. The hinge assembly may include a pair of rotation axes, with the tensioning element extending between the rotation axes. The hinge assembly is preferably located along the frontal plane when the device is in an extension orientation; the tensioning element crosses the frontal plane within the hinge assembly. Further yet, the hinge assembly may define a pair of rotation axes and a main axis generally perpendicular to the rotation axes. The tensioning element may extend between the pair of rotation axes and cross the main axis.

The hinge assembly may include a hinge cover defining an entry aperture through which extends the tensioning element. The entry aperture is preferably located on the second side of the frontal plane, and thereby on a side of the frontal plane opposite to the dynamic calf shell. The hinge cover may define a middle opening with the tensioning element extending into the hinge assembly and anchored at or near the middle opening of the hinge cover.

The adjustment system may include a tightening device arranged for increasing and decreasing tension in the tensioning element. According one variation, the tightening device is a dial-tensioning device arranged for preselected and incremental ratcheting rotational adjustment of the tensioning element. In this variation, the tensioning element is preferably a cable that can be wound and unwound by the dial-tensioning device. In variations, the tightening device comprises straps or other ratcheting means, such as a linear ratchet, or a combination thereof that permits adjusting the tension in the tensioning element.

The brace may further include an elongate strut segment connecting the lower cuff to the hinge assembly and having a guide element orienting the tensioning element from a lateral direction substantially perpendicular to the strut segment to a longitudinal direction generally parallel to the strut segment.

Further yet, the brace may include wings extending from the upper cuff located on the second side of the device toward the first side of the device. A strap carrying a pad, an insert forming in part a shell or combination thereof may extend from the upper cuff on opposed medial and lateral sides thereof and over the wings.

According to an embodiment, the first side of the brace is located on a posterior side of the device and the upper and lower cuffs are located on the first side of the brace, particularly when the brace is configured for treating a PCL. The upper cuff may have a lateral strut extending more proximally than a medial strut, thereby creating a peak at the lateral side of the upper cuff. As noted above, the dynamic calf shell is likewise located on the posterior side. The device further comprises upper and lower straps connected to the upper and lower cuffs, respectively, and extending about the second side of the device located on an anterior side of the device.

The brace may also include a lower tibia shell located on the second side of the device. The lower tibia shell may have a semi-rigid and resilient a generally V-shaped insert. The lower tibia shell is arranged to counteract the dynamic calf shell as the device goes from an extension orientation to a flexion orientation. Moreover, in the orientation as a PCL brace, the lower shell is adapted as a tibial shell such that the V-shaped insert prevents sharp pressure points at a tip of the anterior leg corresponding to the tibia that may occur with a conventional strap, and more evenly distributes pressure on the lower leg due to the counteracting forces of the dynamic calf shell.

The orthopedic device may be adapted to treat other knee infirmities by switching the location of the dynamic calf shell, the orientation of the tensioning element, and the location of the cuffs, shells and straps.

In different embodiments, the orthopedic device is arranged with a dynamic femoral shell that counteracts with a dynamic calf shell, in which both the dynamic femoral and calf shells are secured to one another by the adjustment system. According to one variation, the dynamic femoral shell is located on the anterior side of the frontal plane whereas the dynamic calf shell is located on the posterior side of the frontal plane.

In another embodiment, the orthopedic device is arranged for dynamically treating a knee, with the device having a central axis and a frontal plane parallel to and intersecting the central axis and dividing the device along first and second sides. The device has a medial-lateral plane dividing the device into medial and lateral sides and generally oriented perpendicular to the frontal plane. The device includes a hinge assembly, a frame having first and second frame components spaced apart from and connected to one another by the hinge assembly, a strap system extending between medial and lateral sides of the first frame component, and at least one tensioning element having a first end secured to the strap system and a second end coupled to the hinge assembly, wherein articulation of the hinge assembly pulls the strap system toward the frontal plane by the at least one tensioning element.

The strap system preferably includes a first bracket upon which the first end of a first one of the at least one tensioning element is anchored, and a second bracket upon which a first end of a second one of the at least one tensioning element is anchored. The strap system includes a strap suspended between the first and second brackets, with the strap being adjustable in length between the first and second brackets thereby reducing a length defined between the first and second brackets. A shell may be secured to the strap between the first and second brackets, and arranged for interfacing with anatomy of the user.

The at least one tensioning element is preferably slidably coupled to the first frame component so as to direct the strap system toward the frontal plane. The at least one tensioning element may be arranged to extend over a portion of the first frame component proximate the hinge assembly. The strap system and an anchor point of the connection of the second end of at least one tensioning element at the hinge assembly are preferably located on a first side of the orthopedic device relative to the frontal plane. The second end of the at least one tensioning element may secure to a hinge plate of the hinge assembly.

The at least one tensioning element may include a first tensioning element securing to a first side of the strap system and coupling to a first hinge of the hinge assembly, and a second tensioning element securing to a second side of the strap system and coupling to a second hinge of the hinge assembly. The first and second tensioning elements may be discretely separate from one another.

BRIEF DESCRIPTION OF THE DRAWINGS

These and other features, aspects, and advantages of the present disclosure will become better understood with regard to the following description, appended claims, and accompanying drawings.

FIG. 3 is a perspective view of an embodiment of an orthopedic device for treating a PCL.

FIG. 4 is a front elevational view of the embodiment of FIG. 3.

FIG. 5 is a rear elevational view of the embodiment of FIG. 3.

FIG. 6 is a side elevational view of the embodiment of FIG. 3 in an extension position.

FIG. 7 is a side elevational view of the embodiment of FIG. 3 in a flexion position.

FIG. 11 is an elevational view of the hinge cover for an adjustment mechanism for a dynamic tensioning system in the embodiment of FIG. 3.

FIG. 12 illustrates examples of combinations of the adjustment system and the dynamic tensioning system functioning relative to one another and the level of force exerted on first and second shells as a leg goes from extension into flexion FIG. 13 is an elevational view of a variation of an adjustment mechanism for a dynamic tensioning system in the embodiment of FIG. 3.

FIG. 14 is an elevational view of another variation of an adjustment mechanism for a dynamic tensioning system in the embodiment of FIG. 3.

FIG. 18 is an elevational view of a hinge in the embodiment of FIG. 15.

FIG. 19 is a detail view of a hinge cover taken from an inner perspective in the hinge embodiment of FIG. 18.

FIG. 20 is a detail view of the hinge cover of FIG. 19 taken from an outer perspective.

Figure 1:
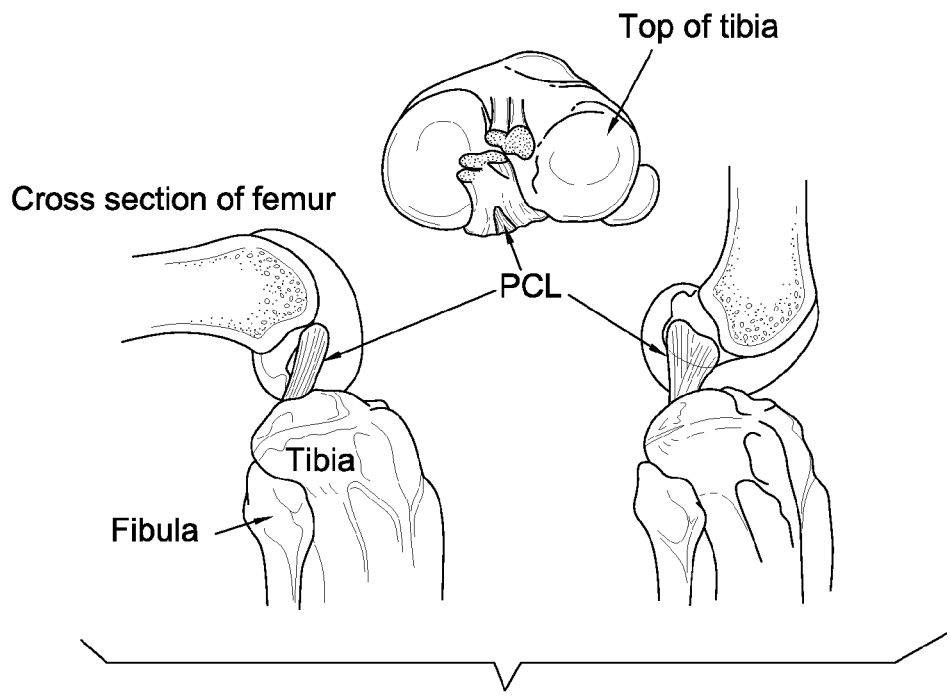
FIG. 1 is a schematic view of the posterior cruciate ligament (PCL) in combination with a femur and tibia.
Figure 2:
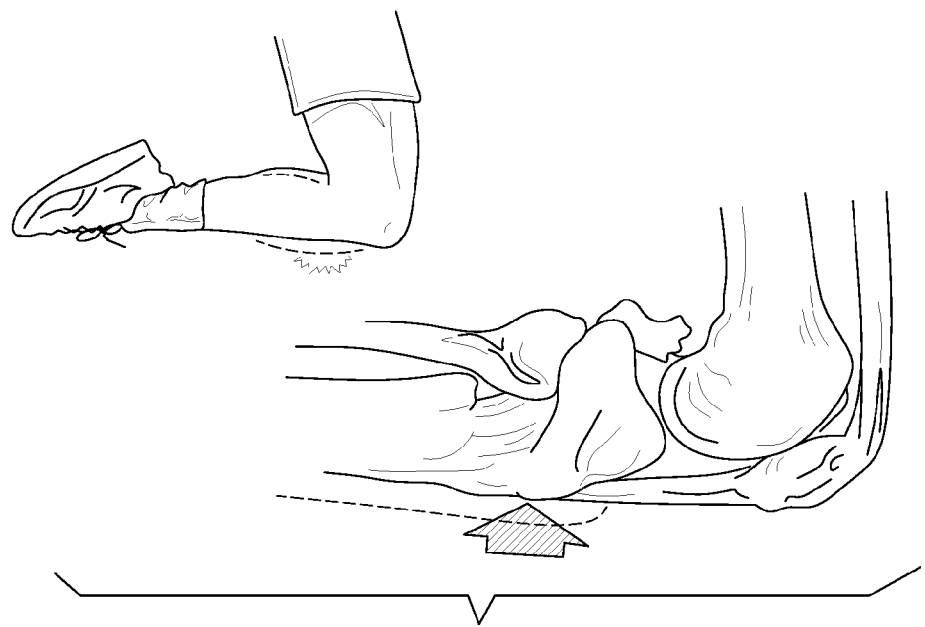
FIG. 2 is a schematic view of a PCL-type injury and a knee during a PCL-type injury.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary embodiments of an orthopedic device and the components thereof, and in no way limit the structures or orientations of an orthopedic device and components thereof according to the present disclosure.

DETAILED DESCRIPTION OF VARIOUS EMBODIMENTS

A. Overview

A better understanding of the different embodiments described herein may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

B. Environment and Context of Embodiments

Numerous orthopedic device embodiments and components for use therewith are described herein, with particular focus given to devices and components directed to the knee joint and surrounding areas. The orthopedic device embodiments may serve in protective, preventative or remedial capacities. While the orthopedic device is described within the context of a preferred embodiment that is directed to treating the posterior cruciate ligament (PCL), many of the features described herein may be extended to orthopedic devices and components that secure other joints and body parts, and to other complications of the knee.

The orthopedic device embodiments and components for use therewith may be dimensioned to accommodate different types, shapes and sizes of human joints and appendages. In addition, embodiments may be modified to orient principal forces exerted by strap systems of the embodiments at any desirable location to secure the device onto a leg in order to stabilize the knee.

The knee joint comprises two joints, lateral and medial, between the femur and tibia, and one arthrodial joint between the patella and femur. The primary movements of the knee comprise flexion, i.e., rearward rotational movement of the tibia relative to the femur, and extension, i.e., forward rotational movement of the tibia relative to the femur.

For explanatory purposes, each orthopedic device embodiment or component thereof described herein may be divided into sections which are denoted by general anatomical terms for the human body. Such anatomical terms are provided to distinguish various elements of the device embodiments from one another, but which are not to be considered to limit the scope of the disclosure.

Each of these terms is used in reference to a human leg, by way of example, which is divided in similar sections with a proximal-distal plane generally extending along the meniscus of the knee between the femur and tibia. The terms "proximal" and "distal" generally refer to locations of the device that correspond to the location of leg relative to the point of attachment of the leg to the body. The terms "upper" and "lower" may be used in combination with "proximal" and "distal" to connote gradations in location of "proximal" and "distal." The location whereat the device corresponds to the knee joint is used herein to generally delimit the proximal and distal sections of the device.

The embodiments of the knee device can also be considered to fall within "anterior" and "posterior" sections by an anterior-posterior plane. The anterior-posterior plane generally corresponds to the coronal or frontal plane of a human leg which lies along the central longitudinal axis of a body. A posterior side or element is therefore located behind this anterior-posterior plane, whereas an anterior side or element is located in front of the anterior-posterior plane.

The terms "inwardly" or "inner" commonly used herein to distinguish the side of the device that may be directed to the posterior side of the device and specifically adjacent to the leg of the wearer of the device. Contrariwise, the terms "outwardly" or "outer" are used to denote the side of the device that is opposite to the inwardly side.

The terms "medial" and "lateral" are relative terms that are generally understood as indicating location with respect to the midsaggital plane or midline. Therefore, elements that are located near the midline are referred to as "medial" and those elements that are further from the midline are considered to be "lateral." The term "central" is used to denote the area along the midline of a joint thereby dividing and sharing regions of the medial and lateral regions.

From these terms, it follows that the anterior section of the device has the following quadrants: (I) proximal-medial, (II) distal-medial, (III) distal-lateral, and (IV) proximal-lateral. The posterior section of the device has the following quadrants: (V) proximal-medial, (VI) distal-medial, (VII) distal-lateral, and (VIII) proximal-lateral. Structural members and features thereof that will fall within one of the quadrants are specifically referenced in relation to such quadrant, either in its entirety or partially.

The device has a center axis X-X when in the extension position which is formed at the intersection of the anterior-posterior plane and the medial-lateral plane.

The terms "rigid" and "flexible" may be used herein to distinguish characteristics of portions of the brace. The term "rigid" is intended to denote that the frame is generally devoid of flexibility. Within the context of frame members that are "rigid," it is intended to indicate that they may break if bent with sufficient force. On the other hand, the term "flexible" is intended to denote that features are capable of repeated bending. The term "resilient" may be used to qualify such flexible features as generally returning to the initially molded shape without permanent deformation.

The anatomical and characteristic terms described herein are not intended to detract from the normal understanding of such terms as readily understood by one of ordinary skill in the art of orthotics. Moreover, the elements of the embodiments described herein are intended to embrace embodiments that generally correspond to the aforementioned anatomical sections. In other words, it is understood that the elements of the device embodiments described herein may deviate from falling exactly within the confines of the aforementioned anatomical sections.

C. Embodiments of the Orthopedic Device

In accordance with a first embodiment illustrated in FIGS. 3-7, the orthopedic device 10 is arranged in the form of a PCL brace. The brace 10 includes an upper or proximal, first cuff 12 and a lower or distal, second cuff 14, each secured to a pair of strut assemblies 19 located on the lateral and medial sides of the brace. Each strut assembly 19 includes an upper or proximal, first strut segment 22 and a lower or distal, second strut segment 24 each connected by a hinge assembly 20. The first and second cuffs 12, 14 are preferably located and secured near the end portions of the first and second strut segments 22, 24 opposite to the hinge assembly 20. In this embodiment, the first and second cuffs 12, 14 are retained stationary to the strut assembly 19.

A first upper strap 38 extends about the anterior side of the brace and connects to the first cuff 12 to effectively form a circumferential loop about the upper end of the brace. Similarly, a second lower strap 40 extends about the posterior side of the brace and connects to the second cuff 14 to effectively form a circumferential loop about the lower end of the brace.

The brace includes a first, anterior dynamic femoral shell 16 located between the first cuff 12 and the hinge assembly 20, and a second, posterior dynamic calf shell 18 located between the second cuff 14 and the hinge assembly 20. The first and second dynamic shells 16, 18 are dynamically secured to an adjustment system 26 that urges the first and second dynamic shells 16, 18 toward one another upon regulation of the adjustment system 26.

The first cuff 12 is preferably arranged on the posterior side of the brace such that it counteracts with the first dynamic shell 16 which is located on the anterior side of the brace. Likewise, the second cuff 14 is preferably arranged on the anterior side of the brace whereas the second dynamic shell 18 is located on the posterior side of the brace. The first cuff 12 is preferably spaced apart from the first dynamic shell by a distance 23, as is the second cuff 14 is preferably spaced apart from the second dynamic shell by a distance 25, the exact distance varying depending on the size of the brace and the length of a wearer's leg.

As illustrated, suitable cuff and shell liners 42 may be included to provide compressive relief to the wearer when straps and tensioning elements are tensioned over a wearer's leg. The hinge assembly 20 may likewise include condyle pads 44 which provide cushioning to the lateral and medial sides of the knee. The cuffs and shells may include ventilation features, such as in a series or pattern of openings 46, so as to allow better breathability when the brace is worn against the leg of the wearer.

The cuffs and shells may be formed from multiple materials or sections having different rigidity or hardness. For example, the core 48 of each dynamic shell may have greater rigidity than an edge portion 50 which may be formed of a less rigid material. Various combinations and methods for forming such multiple material or section cuffs and shells can be found in U.S. Pat. Nos. 7,727,174 and 7,749,183, and U.S. patent application publication no. 2009/0076426, each incorporated herein by reference.

The adjustment system 26 includes a tensioning element 29, such as a cable, that is secured to and adjusted by a tightening device 28 to adjust the length of the cable 29. In a preferred embodiment, the tightening device 28 is a dial-tensioning device 28 arranged for incremental and preselected adjustment in the tension of the tensioning element. The dial-tensioning device may be rotated clockwise to decrease the length of the cable 29 and thereby increase the overall tension of the adjustment system 20. To decrease the overall tension of the adjustment system, the dial-tensioning device 28 may be rotated counterclockwise to increase the length of the cable 29. The dial-tensioning device may be provided by BOA Technology Inc. and is also described in US 2009/0287128, which is incorporated herein by reference and belongs to the assignee of this disclosure. The tightening device is not limited to the example provided above, and may comprise straps, cables, brackets, hook and loop fastener systems, or ratcheting means, such as a linear, ladder or buckle ratchet, or a combination thereof, that permits adjusting the tension in the tensioning element The first and second dynamic shells 16, 18 are slidingly and pivotally secured to the strut assembly 19 along slots formed by the first and second dynamic shells 16, 18. As the dial-tensioning device 28 is regulated to adjust the tension in the cable 29, the first and second dynamic shells 16, 18 are urged toward one another, while sliding along the slots, and effectively moving relative to the strut assembly 19. The dynamic shells are also able to pivot relative to the strut assemblies in order to accommodate flexion of the knee and leg.

The dial-tensioning device 28 is preferably centrally secured to the frontal or outer surface of the first dynamic shell 16, and the cable 29 extends from both lateral and medial sides of the dial-tensioning device 28 to the first strut segments 22. The upper dynamic shell 16 may include upper guide channels 34 that maintain the direction of the cable 29 toward the strut segments 22. The cable 29 is received on the first strut segments 22 by upper guides 30 which in turn direct the cable 29 toward the hinge assembly 20. The cable 29 passes through the hinge assembly 20 and extends to lower guides 32 located on the second strut segments 24 which in turn direct the cable 29 about the second dynamic shell 18 and through a lower guide channel 36 located or formed on the frontal or outer surface of the second dynamic shell 18.

It will be noted that ends of the cable 29 are preferably retained within the dial-tensioning device 28 and the portion of the cable 29 outside the dial-tensioning device 28 extends continuously about the brace without interruption. Tensioning of the cable 29 by the dial-tensioning device 28 occurs simultaneously across both the first and second dynamic shells 16, 18. While this is the preferred embodiment, it will be noted that the orthopedic device is not limited to a single cable or a single dial tensioner, but it is envisioned that multiple cables and dial tensioners may be used to urge or move the first and second dynamic shells relative to the strut assembly.

Figure 8:
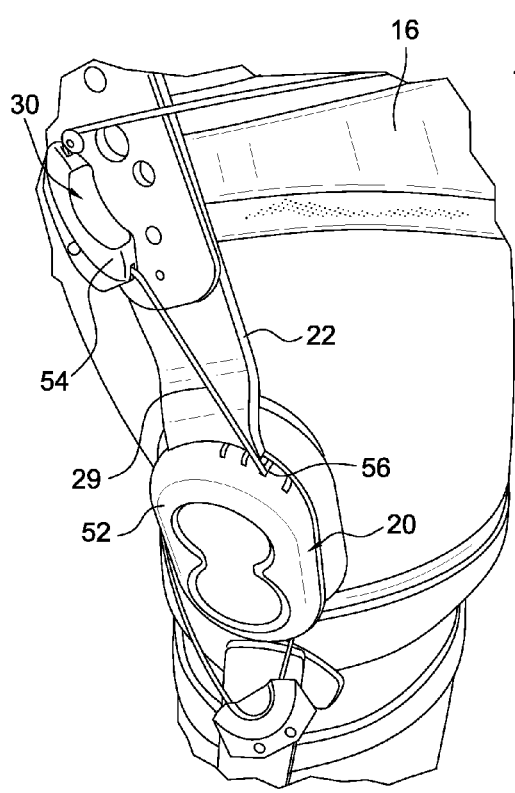
FIG. 8 is a schematic detailed view showing a hinge assembly and tensioning element of the embodiment of FIG. 3 in an extension position from an upper perspective.
Figure 9:
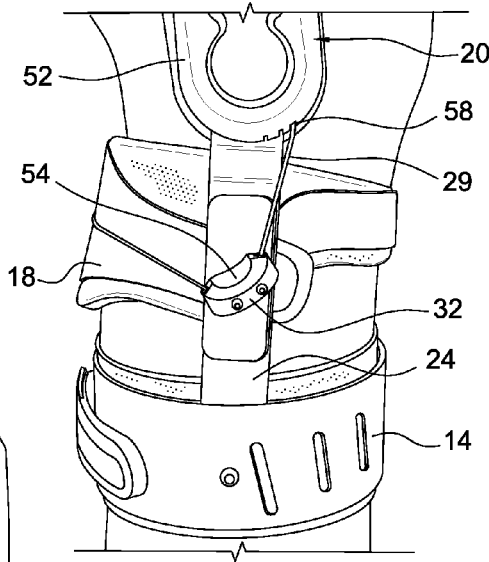
FIG. 9 is a detailed view of a variation of the embodiment of FIG. 3 in an extension position from a lower perspective.
Figure 10:
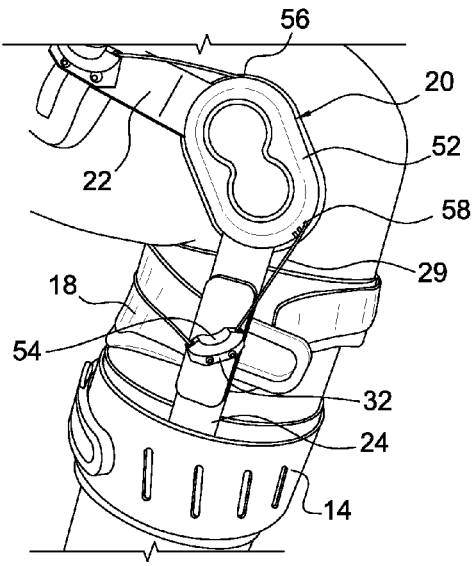
FIG. 10 is a detailed view of a variation of the embodiment of FIG. 3 in a flexion position.

FIGS. 8-10 exemplify the cable 29 and hinge assembly 20 from an outer perspective of the brace. In reference to FIG. 8, the guide 30 is shown as having a guide route 54 that directs the cable 29 extending from the frontal surface of the first dynamic shell 16 along the first strut segment 22 and into the hinge assembly 20 via one of a series of upper openings 56 formed in part by a face plate 52 of the hinge assembly 20. FIG. 9 shows the cable 29 exiting the hinge assembly 20 from one of a series of lower openings 58 formed by the face plate 52. FIG. 10 shows the travel of the cable 29 relative to the strut assembly when the knee is placed into flexion, and can be contrasted from the extension position brace in FIGS. 8 and 9.

FIGS. 11, 13 and 14 show different dynamic tightening device embodiments of the internal aspects of how the hinge assembly may dynamically engage the cable. First, in observing FIG. 11, this tightening device relies on the hinge cover 52 as forming a plurality of fixed channel routes 60, 62, 64, 66 extending along elongate channels 68 and opening from the hinge assembly at the upper and lower openings 56, 58. For example, the cable 29 enters at a corresponding one of the upper openings 56, enters the channel route 60 so as to be retained by the corresponding elongate channel 68 and departs from the hinge assembly from a corresponding one of the lower openings 58. The hinge cover 52 includes a cavity 70 which may receive the actual hinge mechanism used to secure the first and second strut segments to one another and simulate movement of the knee.

The channel routes 60, 62, 64, 66 are located on the anterior side of the hinge cover 52, and are offset relative to the hinge center demarcated by a longitudinal hinge main axis Y-Y. The relationship of the channel routes relative to the hinge center determines the level of force generated by the adjustment system and hence the level of force exerted by the first and second dynamic shells on the tibia of the wearer of the brace. The placement of where the cable runs with respect to the hinge center will vary the excursion of the cable and thus impart a change in the dynamic force it can impart on the leg.

It follows that the farther in front of the hinge axis, the greater the excursion of the cable and thus the greater the dynamic force it can exert on the second dynamic shell and the first dynamic shell simultaneously, thus creating a higher PCL stabilizing force for the same range of motion. The dynamic force achieved by placement of the cable relative to the hinge center is separate and distinct from merely tensioning the cable by the dial tensioner.

As shown in FIG. 7, in comparison to FIG. 6, the dynamic shells may be tightened by the adjustment system, when the brace is in either extension or flexion, as evidenced by force arrows A, B. When the knee goes into flexion, rotational forces or dynamic forces arise by the dynamic tightening device, so that if both the adjustment system is tensioned and the dynamic tightening device is relied upon by mounting the cable forward the hinge center, forces C, D in addition to forces A, B push the tibia forward to dynamically assist knee laxity and the PCL in general.

FIG. 12 illustrates examples of how combinations of the adjustment system and the dynamic tensioning system function relative to one another and the level of force exerted on first and second dynamic shells as a leg goes from extension into flexion. In the first arrangement of Example 1, the cable is placed in a channel route farthest from the hinge center, and the adjustment system is tensioned. This combination results in high dynamic force exerted on the tibia in connection to the femur by the first and second dynamic shells. However, the starting tension is also the highest as there is already an existing force on the leg due to the tension in the adjustment system before the leg goes into flexion.

Turning to Example 2, the cable is placed in a channel route again farthest from the hinge center; however the adjustment system is not tensioned and does not effectively exert any tension on the leg when the leg is in extension. A high force is again exerted on the leg as the leg goes into flexion however the force is less than in Example 1 due to there being no tension on the leg due to the adjustment system before flexion.

Referring to Example 3, the cable is placed in a channel route closer to the hinge center, and again the adjustment system is not tensioned and does not effectively exert any tension on the leg when the leg is in extension. A lower force than in Example 2 is exerted on the leg.

Lastly, in Example 4, the cable is placed along the hinge center and there is no initial tension exerted by the adjustment system. From this configuration, there is little or no dynamic tensioning exerted by the dynamic tensioning system as the leg goes into flexion.

When dosing the brace on the leg of a wearer, certain considerations are made regarding the dosing including the knee laxity, the activity of the wearer, and the size of the wearer's leg and anatomy. The brace may be adapted to permit the practitioner to set the tension on the brace, particularly by the adjustment system, the dynamic tensioning system, or both, and to assure that the wearer has some visual or audio notification of correct adjustment of the brace.

One option for assuring correct dosage of the brace is to set a series of indicia, such as numbers or symbols, on the cable that can be relied upon to match a certain load that the brace may exert on the wearer from extension and a range of flexion. Another option is to provide a load sensor in the cable that indicates through audio or visually whether a load on the knee and leg is too high. Yet another option is to provide sensors that track the distance of the cable or the relationship among the dynamic shells so that adjustment of the cable or shells does not exceed a certain threshold.

FIG. 13 shows another embodiment of a dynamic tightening device 53 having a movable cam element 74 slide mounted on a plate 72. The cam element 74 moves between and is retained from upward or downward movement by upper and lower bearings or rivets 76, 78 located along the hinge axis Y-Y. The cam element may slidingly engage the bearings, or alternatively the bearings are actually rivets provided irrespective to any motion of the cam element. The plate 72 includes at least one slot 82 permitting sliding movement of the cam element 74 relative to the plate 72. At least one fastener 84 locks the cam element 74 in position so as to position a face 86 of the cam element 74 for receiving the cable 29. This embodiment permits a multitude of positions of the cam element and allows for drawing the cable away from the hinge axis, only to be limited by the length of the arm.

FIG. 14 shows another embodiment wherein a rotatable cam element 88 is positioned about the bearing 78. The cam element 88 may be mounted about either of the bearings 76, 78 so as to draw the cable 29 away from the hinge center. The cam element 88 includes a face 90 about which the cable extends, and a fastener 92 is used to secure the bearing 78 and cam element 88 in a fixed position.

It will be noted that the device is not limited to an actual hinge mechanism for securing the first and second strut segments to one another and to simulate movements of the knee. Instead, the embodiments in FIGS. 11, 13 and 14 are primarily only directed to means for dynamically engaging the cable to the hinge assembly.

Figure 15:
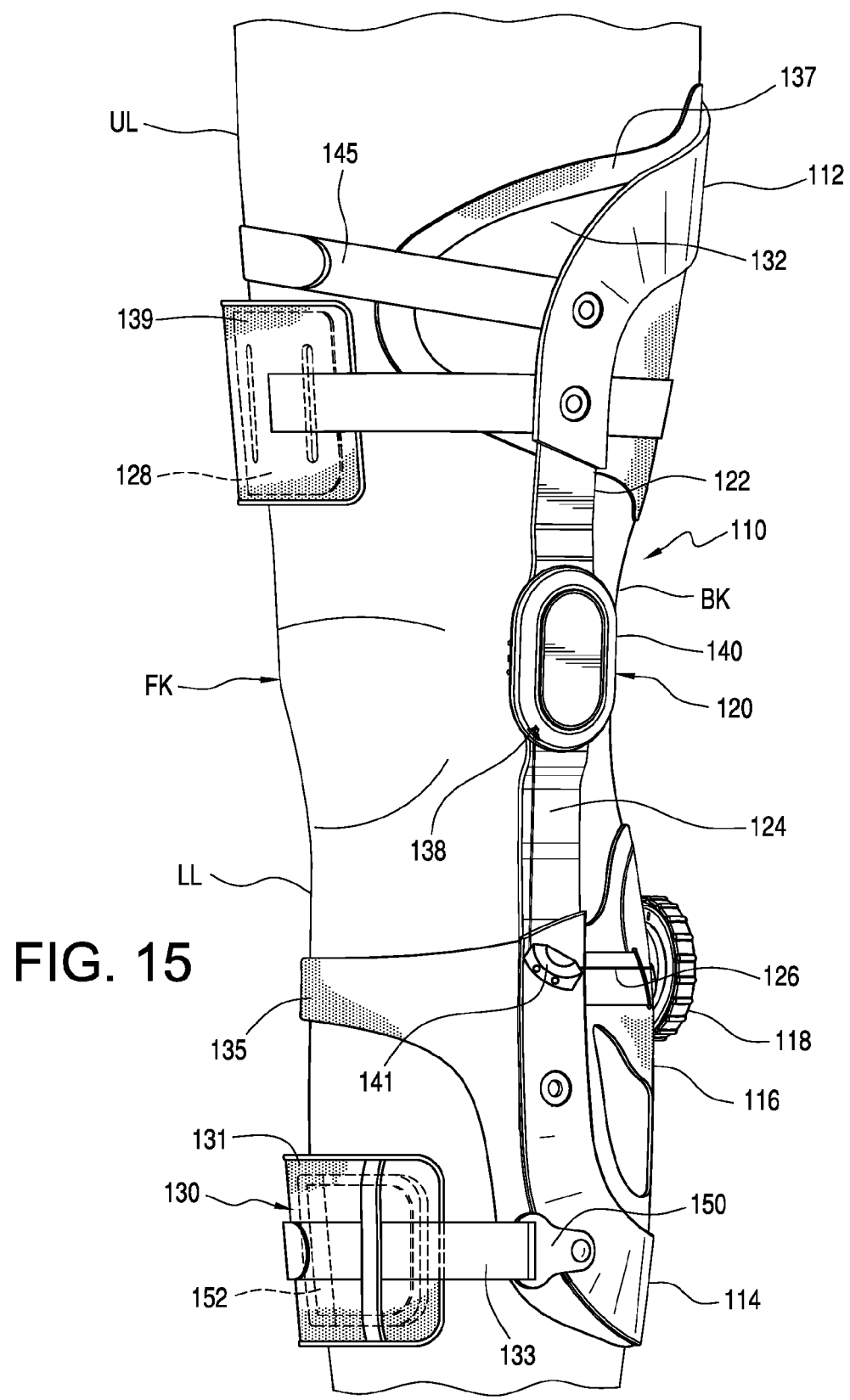
FIG. 15 is a perspective view of another embodiment of an orthopedic device for treating a PCL.
Figure 17:
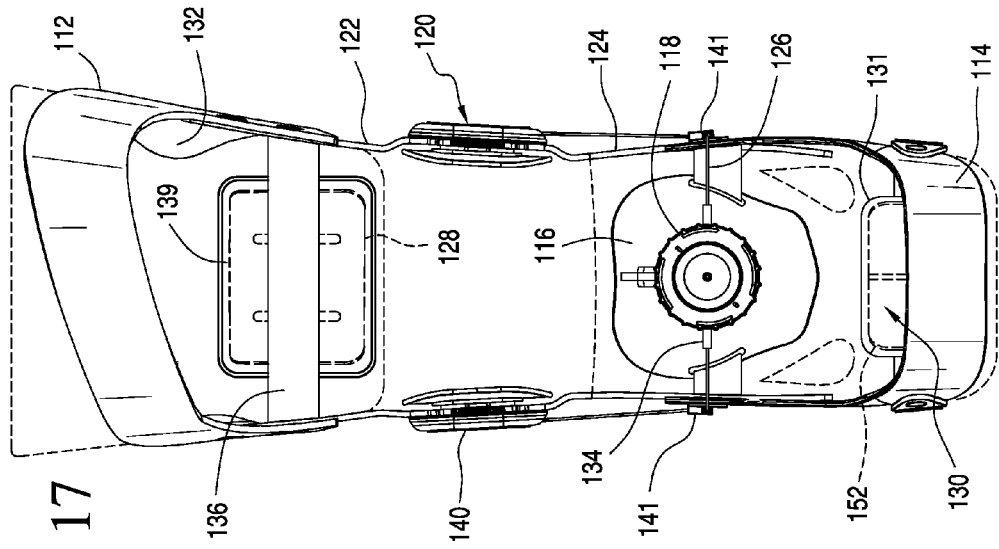
FIG. 17 is a front elevational view of the embodiment of FIG. 15 in an extension position.
Figure 16:
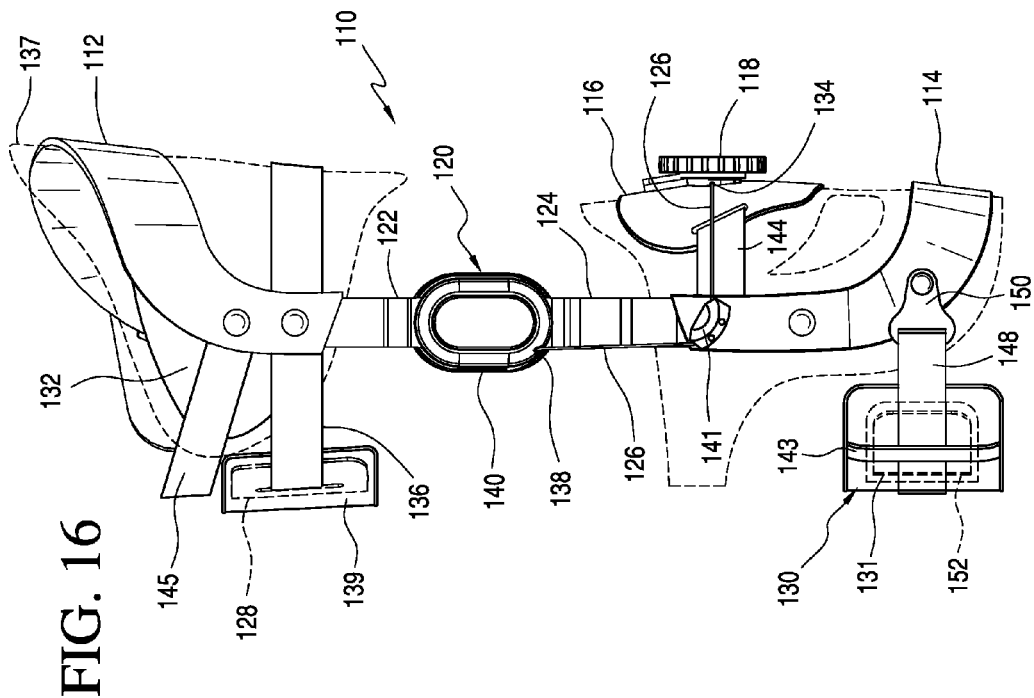
FIG. 16 is a side elevational view of the embodiment of FIG. 15 in an extension position.

FIGS. 15-17 illustrate another embodiment of the orthopedic device according to the disclosure in the form of a PCL brace. The embodiment includes a frame having an upper cuff 112 and a lower cuff 114 spaced apart from and connected by a hinge 120, between the front knee FK and back knee BK, by upper and lower struts 122, 124. Both the upper and lower cuffs 112, 114 are arranged on the posterior side of the device on both the upper leg UL and lower leg LL, respectively, in part due to ease donning of the device, and also in supporting the leg and maintaining the brace on the leg in view of the adjustment system 118.

The upper cuff 112 has a peak side generally located on the posterior lateral side and formed in part by a lateral segment, which is higher than a medial segment and linked by a sloping segment. The arrangement of the upper cuff is advantageous in that it contributes to medial and lateral stability as the lever or lateral segment increases in size. The arrangement also allows for coverage of more femoral and thigh soft tissue for better distributing pressure over the upper leg UL. The lower height of the medial segment provides for a lower profile on the medial side as it is more desired for improved comfort between soft tissue for right and left legs, thereby minimizing the side of the cuff to avoid bumping the medial side of the other leg.

In order to counteract the upper and lower cuffs 112, 114, the brace includes an upper femoral shell 128 connected to the upper strut 122 by a strap 136 and covered with padding 139, and a lower tibial shell 130 including a generally V-shaped insert 152 and is connected to the lower cuff 114 or lower strut 124 by a strap 148 and a bracket 150 such as a D-ring. The lower tibial shell may likewise be covered with padding 131. A padding wrap 135 preferably circumferentially extends around the lower leg LL and extends between a dynamic calf shell 116 and the lower cuff 114. The padding wrap 135 may be adjustable and tightenable over the lower leg, and may be integrally connected between the locations corresponding to the dynamic shell and the lower cuff.

The brace 110 includes upper wings 132 extending generally from the upper cuff 112 and projecting toward and wrapping about at least a portion of the anterior side of the brace. Padding 137 is provided in combination with the wings 132, and the wings are more rigid and resilient than the padding 137. A strap 145 may extend over the wings 132 or connect to the wings so as to extend about the anterior side of the brace. Alternatively, the strap 145 may be connected to the padding 137 or be formed as part of the padding 137 so as to define a wrap about the upper leg.

The wings are arranged to cover more surface of the upper leg, particularly on the anterior side of the leg than a simple strap and work to contain soft tissue around the femur, and prevent the strap from digging into the soft tissue. In many conventional braces, straps have a tendency to submerge or press deeply into soft tissue of the thigh which causes discomfort and may lead to less stable attachment to the thigh. The wings are particularly arranged on at least the medial and lateral sides, and reaching into a portion of the anterior side of the thigh to avoid locations at which conventional straps are prone to pressing deeply into the soft tissue.

The adjustment system 118 is arranged on the dynamic calf shell 116, which is generally arranged over the upper and fleshy portion of a wearer's posterior calf. The dynamic shell 116 is connected to the lower strut 124 by a strap 144, and may be pivotally connected or connected in a fixed orientation relative to the lower strut 124.

The adjustment system 118 includes a tensioning element 126, such as the aforementioned cable in other embodiments described herein. When the brace is arranged in extension, the cable 126 extends from the tightening device 118 in a generally lateral direction by extending through guides 134 located on the dynamic shell 116, and is redirected in a generally longitudinal direction by guides 141 located on the lower strut 124 to an aperture 138 on a hinge cover 140 of the hinge 120. The adjustment system may be arranged in accordance with any of the examples described herein.

The guides 134 may comprise any number of types of guides for routing the cable 126 to the lower strut 124. It is preferable that the cable 126 is arranged laterally relative to the lower strut 124 and received by the guide or series of guides 141 located on the lower strut 124. The guides 134, 141 may comprise tubes, brackets, channels and any other type of form that will permit the cable to be directed in a straight orientation (in the case of the guides 134) and curved or reoriented orientation (in the case of the guides 141) located on the struts which essentially direct the cable in a direction perpendicular to the guides 134. While the embodiment of FIG. 16 shows the cable 126 as generally running alongside an anterior side of the lower strut 124 as it approaches the hinge 120, it will be noted that additional guides may be employed along the lower strut to maintain the cable in this orientation, or in an alternative orientation.

Referring to FIGS. 18-20, the hinge assembly 120 includes hinge head portions 158, 160 having rotational axes A, B aligned along a vertical or main axis Y-Y of the hinge assembly. The hinge cover 140 includes an entry aperture 138 located along a lower corner on the anterior side of the hinge 120 and the main axis through which extends the cable 126. The cable is anchored at anchor point 156 on the hinge cover 140. The cable 126 is arranged to extend between the rotational axes A, B, and at least over the lower axis B so that as the hinge goes from extension to flexion, the cable 126 is pulled over the lower axis B.

The relationship to the entry aperture and the axis is similar to the embodiments discussed above in connection with the embodiments of FIGS. 11, 13 and 14, and the discussion in connection with the graph of FIG. 12. In other words, placement of the entry aperture impacts the force level exerted by the dynamic shell due to the length of the tensioning element.

Taken from the inner side of the hinge cover in FIG. 19, the hinge cover 140 includes a channel 166 through which the cable 126 extends to a hole 168 communicating with the exterior side of the hinge cover 140. FIG. 20 shows the cable 126 as having an anchor 156 which fits within a slot 154 formed on the exterior side of the hinge cover so as to retain the upper end of the cable 126 to the hinge 120.

Figure 21:
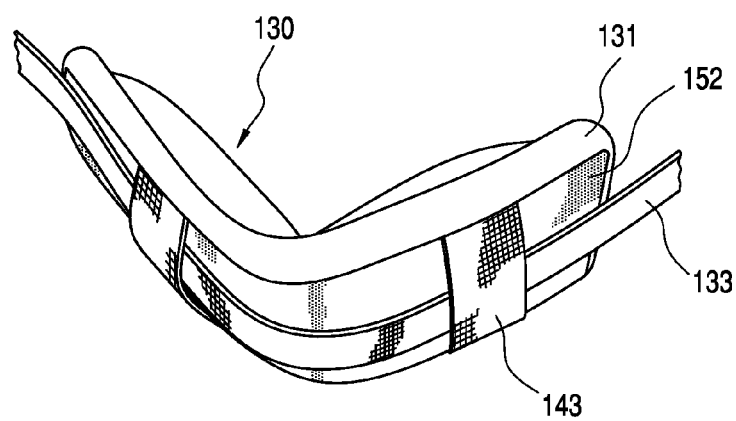
FIG. 21 is a detailed perspective view of the lower tibia shell in FIG. 15.

FIG. 21 depicts the lower tibia shell 130 that is adapted to more evenly distribute loads on the anterior tibia. The tibia shell 130 includes the semi-rigid or flexible insert 152 that generally maintains a V-shape. The padding 131 is provided on the rear side of the lower tibia shell 130 and is adapted to be placed adjacent to the anterior tibia of the wearer. The strap 133 is intended to extend about the front side of the lower tibia shell 130 and is slidably retained to the lower tibia shell 130 by loops 143 which allows for the strap to be adjusted while stably maintaining the lower tibia shell on the wearer's leg. The strap 133 is coupled to the lower cuff 114 by a bracket 150.

Figure 22:
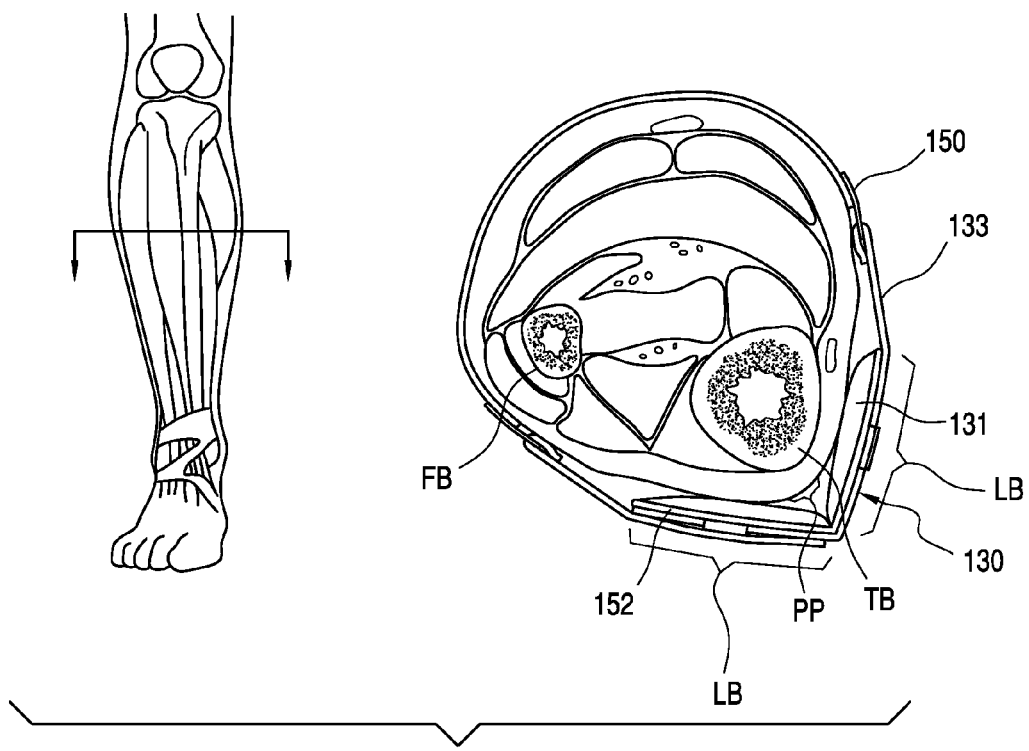
FIG. 22 is a schematic view showing force exerted on the lower leg by the tibia shell of FIG. 21.

As schematically shown in FIG. 22, the V-shape of the insert 152 is advantageous in that it avoids forming a direct pressure point PP on the anterior tibia bone TB, particularly in view of the counteracting forces due to the anterior pressure applied by the dynamic shell as the knee goes into flexion. The pressure point PP on the anterior tip can create undue pressure on the tibia bone TB and therefore harm the wearer. The shape of the insert 152 and thus the lower tibial shell 130 therefore forms a greater load bearing LB area on both sides of the pressure point PP, avoiding the tip of the anterior tibia bone TB, and comfortably allows the strap 133 to extend about the wearer's fibula bone FB and the tibia bone TB by creating more surface area on the sides of the tibia bone TB.

Figure 23:
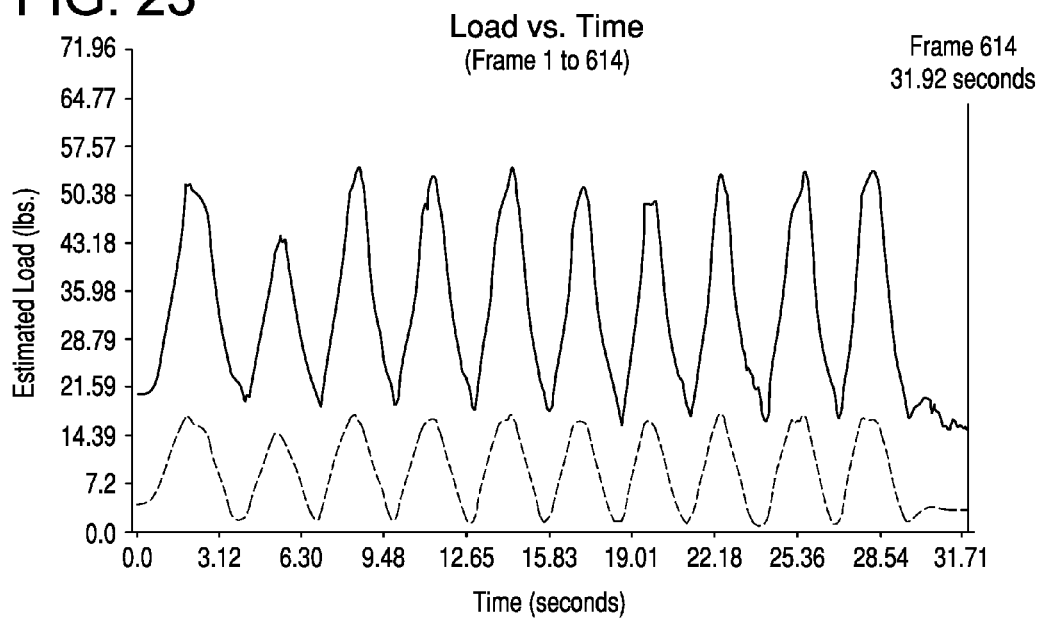
FIG. 23 is a graph depicting the load versus time as the knee goes from extension to flexion and so forth.
Figure 24:
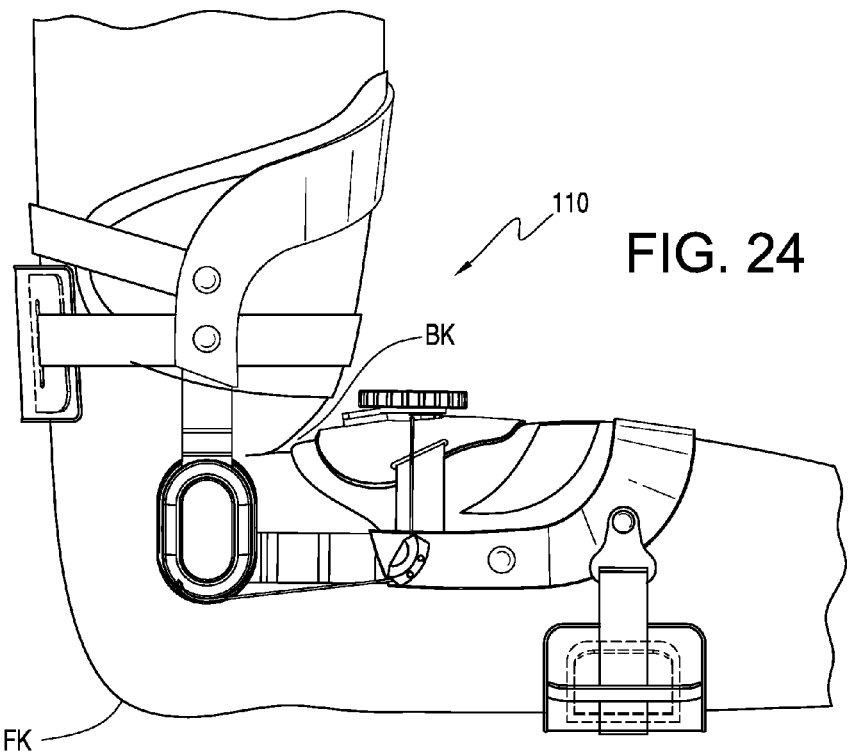
FIG. 24 is an exemplary view showing the orthopedic device of FIG. 15 in flexion.

In referring to FIG. 23, a chart shows the calf loading (anteriorly directed estimated load on the posterior proximal tibia) and the thigh loading (posteriorly directed counter force on the distal anterior femur) as the knee goes from extension to flexion and back. The upper curve in solid line represents the calf and the lower curve represents the thigh. The loading is plotted against time. Peak loading occurs at peak flexion, which is limited to approximately 90°, as shown in front knee FK and back knee BK with the brace 110 in flexion in FIG. 24. From the curves, it follows that as the cable shortens when the knee flexes, there is a generation of increased calf loads that in turn urges the tibia anteriorly to compensate for an impaired PCL therefore dynamically treating the knee.

Figures 25A, 25B:
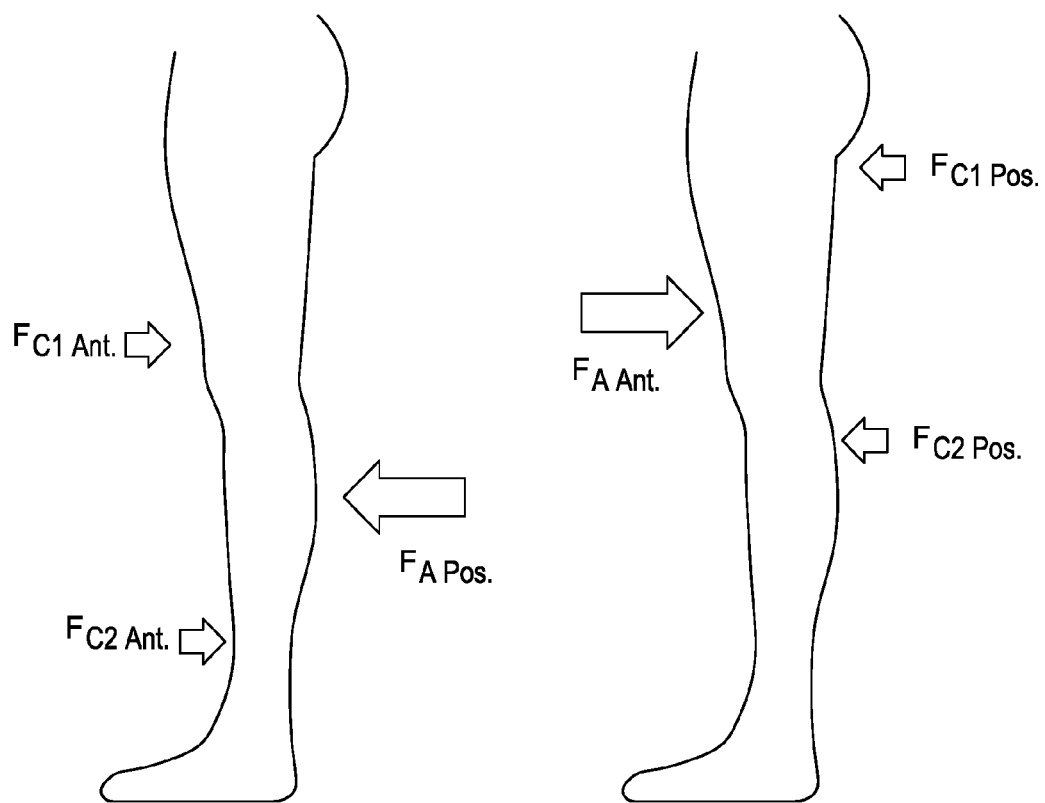
FIGS. 25A and 25B are schematic views showing femoral and tibial force loading using variations of the orthopedic device according to the disclosure.

FIG. 25A shows a force diagram of the orthopedic device 110, whereby the applied or dynamic posterior force $F_{A\ Pos.}$ is applied by the dynamic shell 116 by tensioning of the cable 126 via the adjustment system 118, and adjusting relative to the articulation of the hinge 120. The dynamic posterior force $F_{A\ Pos.}$ is directed anteriorly. The upper femoral shell 128 and the lower femoral shell 130 resist the dynamic force $F_{A\ Pos.}$ with counterforces $F_{C1\ Ant.}$ and $F_{C2\ Ant.}$ respectively, directed posteriorly. The counterforces $F_{C1\ Ant.}$ and $F_{C2\ Ant.}$ are located and exerted against the anterior femur or thigh, and lower tibia or shin, respectively, of the user.

FIG. 25B exemplifies a variation of the orthopedic device 110 of FIG. 25A, and the accompanying force loading. In the embodiment of FIG. 25B, the applied or dynamic force $F_{A\ Ant.}$ is arranged to exert posteriorly from an anterior side of the orthopedic device. Counterforces $F_{C1\ Pos.}$ and $F_{C2\ Pos.}$ are arranged to exert anteriorly directed forces from the posterior side of the orthopedic device. Of note, the applied or dynamic force is located proximally or above the knee and exerted against the femur or thigh of the user. The rearrangement of forces in FIG. 25B may result from switching location of the components of the orthopedic device of FIG. 15.

As the applied or dynamic force is applied above the knee in the variation of FIG. 25A, the counterforces are balanced by being generally located or exerting at higher or more proximal locations than in the embodiment of FIG. 25A. Specifically, the first counterforce $F_{C1\ Pos.}$ is located just short of the user's buttocks on the posterior side of the upper leg. The second counterforce $F_{C1\ Pos.}$ is just located below the posterior knee, in part due to the necessity for articulation of the hinge, and exerts against the calf of the user.

As shown in both FIGS. 25A and 25B, the applied or dynamic force is generally located between equidistant of the counterforces. While the orthopedic device is not limited to this arrangement, the equidistant relationship allows for more even distribution of the counterforces relative to the applied or dynamic force.

Figure 26:
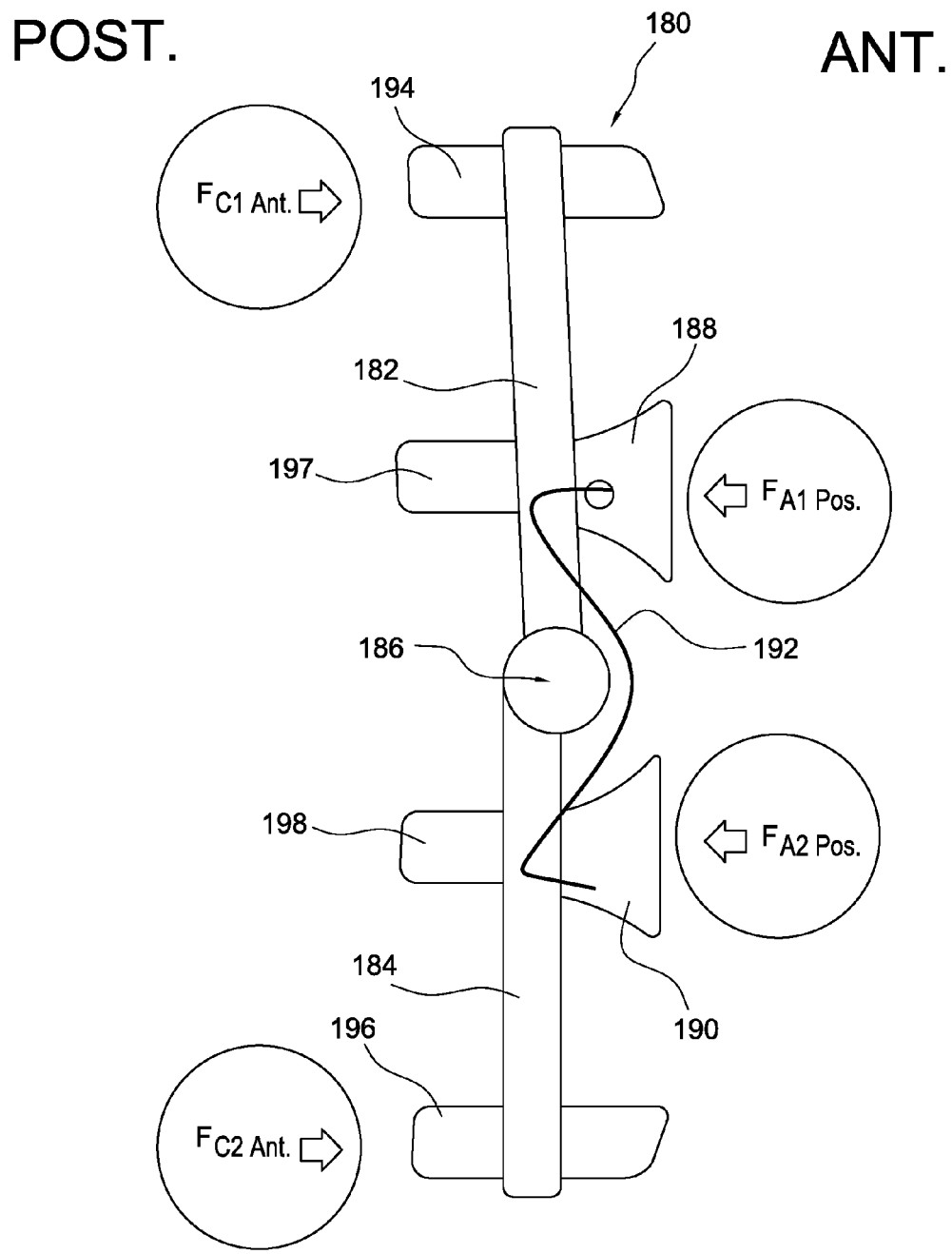
FIG. 26 is a schematic view of another embodiment of the orthopedic device arranged for dual anterior loading.

FIG. 26 exemplifies another embodiment of the orthopedic device 180 including two components 188, 190 arranged for applying an applied or dynamic force on the leg of a user. According to this embodiment, the components 188, 190 are located on the anterior side of the orthopedic device and connected to first or upper and second or lower struts 182, 184 connected to one another by a hinge 186. Of note, the hinges may be located on lateral and medial sides of the orthopedic device. A tensioning element or cable 192 connects to the components 188, 190, and can be tensioned according to articulation of the hinge 186. The cable 192 may be connected to the hinge 186 in a variety of ways, including running through a retaining element, such as a channel or bracket, located on an anterior side of the hinge 186 so that the cable tensions as the first and second struts 182, 184 articulate relative to one another by the hinge 186.

The orthopedic device 180 preferably includes device elements such as straps, shells, a frame or cuffs 194, 196 for counteracting the applied or dynamic forces $F_{A1\ Pos.}$ and $F_{A2\ Pos.}$ exerted by the components from the anterior side of the orthopedic device and directed posteriorly. The elements 194, 196 preferably provide counterforces $F_{C1\ Ant.}$ and $F_{C2\ Ant.}$ directed anteriorly to counteract the applied or dynamic force. Suitable other device features 197, 198, such as straps, aid in maintaining the orthopedic device on the leg of the user.

FIGS. 27-30 exemplify another embodiment of an orthopedic device 200 relying on the interaction of a tensioning element with a hinge for applying a dynamic force on the leg of user. The orthopedic device is arranged for treating patellafemoral pain and osteoarthritis of the knee.

Figure 27:
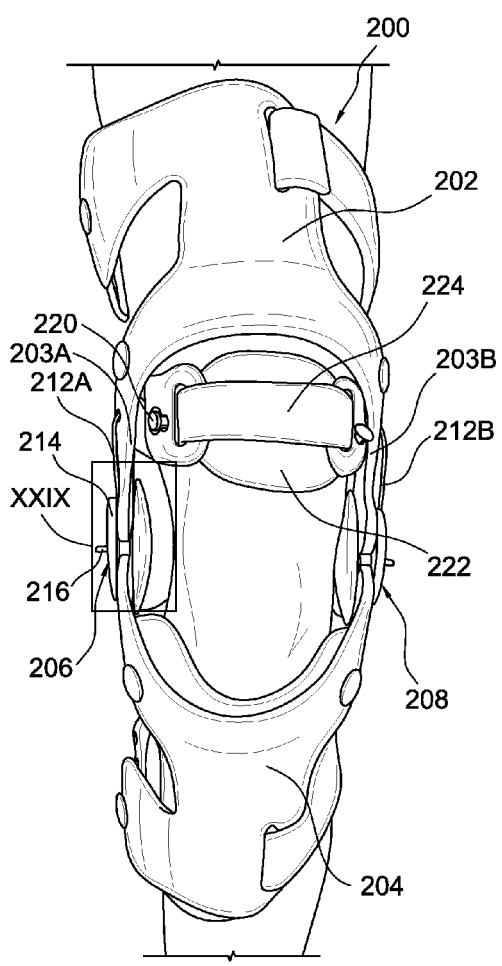
FIG. 27 is a front elevational view showing another embodiment of the orthopedic device.
Figure 28:
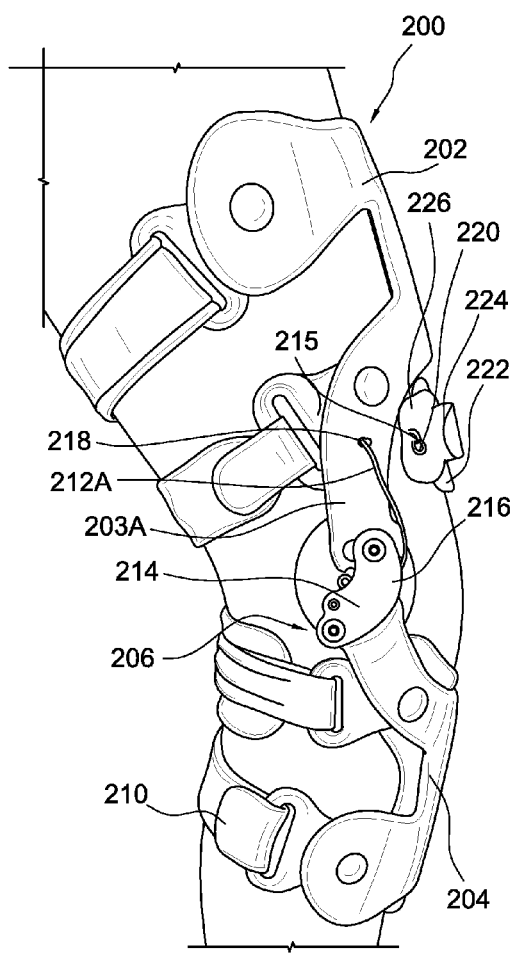
FIG. 28 is a side elevational view showing the embodiment of FIG. 27.

As shown in FIGS. 27 and 28, the orthopedic device 200 includes an upper frame component 202 and a lower frame component 204 connected to one another by hinges 206, 208. The upper frame component 202 includes first and second strut portions 203A, 203B, generally corresponding to lateral or medial sides of the orthopedic device. A plurality of straps 210 are arranged for maintaining the orthopedic device 200 on the leg of the user.

The upper and lower frame components, as well as the hinges, may have a construction similar to the embodiments described in U.S. Pat. No. D577,828, granted Sep. 30, 2008 and U.S. patent application publication no. 2008/0195013, published Aug. 14, 2008, incorporated herein by reference. As will be discussed, an advantage to the embodiment of the orthopedic device 200 is that various components thereof can be adapted to retrofit various orthopedic devices having different brace frame components and contours, particularly those orthopedic devices having a double-upright configuration.

Referring to FIG. 28, the orthopedic device 200 includes a tensioning element 212A, in a preferred form of a cable, having a first end securing to a shell 222 and a second end securing to the hinge 206. While FIG. 28 shows only one side of the orthopedic device with the first strut 203A and the hinge 206, FIG. 30 exemplifies how the opposing side of the orthopedic device may be arranged similarly with the second strut 203B and the hinge 208, along with a corresponding tensioning element 212B that secures to the shell 222.

The first end 215 of the tensioning element 212A is anchored at an anchor point 220 on a first bracket 226 securing to the shell 222. The tensioning element 212A is movably secured to the first strut 203A so as to allow it to adjust relative to movement by the upper frame component 202 relative to the lower frame component 204. For example, in the illustrated embodiment of FIG. 28, an opening 218 is formed on the first strut 203A through which the tensioning element 212A extends and slidably couples to the upper frame component 202. By slidably coupling to the upper frame component, the tensioning element can move relative to the upper frame component as the hinge articulates while being urged against the upper frame component so as to pull or redirect the strap system relative to the upper frame component. Alternatively, the tensioning element 212A may extend through a guide or suitable element as described in connection with the embodiment of FIG. 16.

Figure 29:
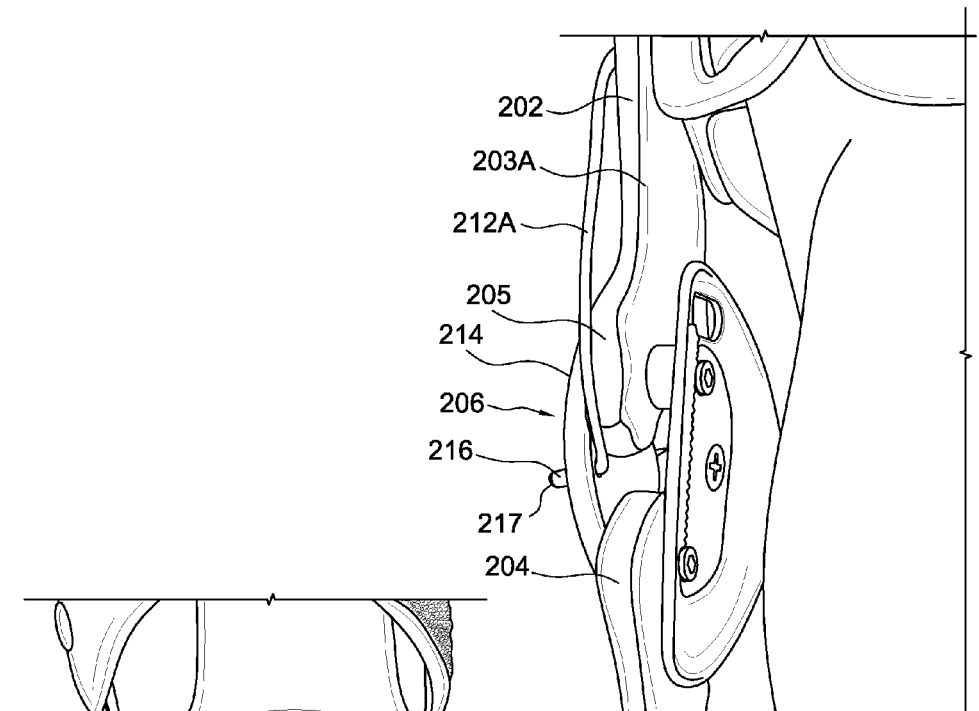
FIG. 29 is a detail view showing detail XXIX in FIG. 27.

The second end 216 of the tensioning element 212 secures to a hinge plate 214 of the hinge 206, preferably at an anterior side or end. As shown in FIG. 29, the tensioning element 212A extends over an end portion 205 of the first strut 203A along the anterior side of the orthopedic device, to aid in tensioning of the tensioning element 212A. The second end 216 of the tensioning element 212A may include a bracket or other suitable element 217 maintaining the tensioning element 212A secured to the hinge plate 214.

The orthopedic device is not limited to the second end 216 securing to the hinge plate 214, but may be secured to any of hinge components that remain stationary or translate relative to rotation of the first and second struts 203A, 203B as structures of hinges may vary from orthopedic device to orthopedic device.

Figure 30:
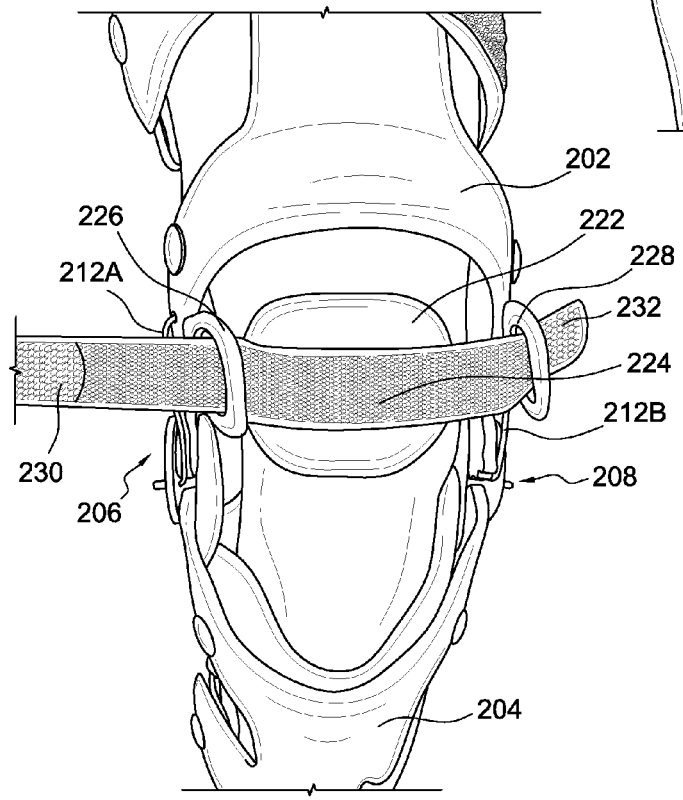
FIG. 30 is a front elevational view showing the embodiment of FIG. 27 being adjusted.

Referring to FIG. 30, a strap 224 secures to the first bracket 226 and a second bracket 228 similarly arranged as the first bracket 226, of which the first and second brackets 226, 228 carry the first ends of the tensioning elements 212A, 212B. The strap and the brackets form at least part of or the entirety of a strap system. The strap system may be provided alone to urge against the upper knee of the user, or alternatively the shell may be selectively applied thereon.

The shell 222 is preferably carried by the strap 224, and may be adjustable at positions between the first and second brackets along the length of the strap therebetween. The strap 224 has first and second ends 230, 232 which are securable to one another to pull the first and second brackets 226, 228 toward one another and tighten over the upper knee of a user, to apply pressure on the leg, beyond articulation of the hinges 206, 208. The strap ends may secure to one another by a hook and loop system, whereby various portions of the strap have section of hook material and hook-receivable material, or other suitable means for securing the strap ends to one another or other portions of the strap (i.e., middle portion between the first and second ends). The strap enables coarse adjustment of a distance between the first and second brackets. It follows that as the hinges and hence the upper and lower frame components, articulate, the tensioning elements 212A, 212B pull the shell 222 toward the upper knee or leg of the user to apply pressure beyond pressure from tightening of the strap between the brackets 226, 228.

The concept of the tensioning device, and shell and strap system of this embodiment may be adapted to a variety of configurations, for exerting a load on the leg or knee of a user according to articulation of the hinge. The orthopedic device may be arranged with an adjustment device, as in other embodiments described herein.

Orthopedic devices may be provided with a strap system having opposing brackets upon which a strap adjustably secures and carries a shell. The brackets are held by tensioning elements connected to one of the upper and lower frame components, and coupled to the hinge so the tensioning elements urge the shell and strap system in a direction relative to the upper and lower frame components upon articulation of the hinges.

The frame for the aforementioned embodiments is a custom brace, commonly created from a model derived from a cast, and from measurements or scan of the user's leg. It is possible to alter the dimensions of the model to deviate from the actual users dimensions. The frame can have corrective varus/valgus contouring for the user for treating osteoarthritis. The frame may be contoured with up to 7°, preferably +/−3°, of varus or valgus correction, to treat osteoarthritis and ligament instability.

If the sagittal plane tibiofemoral angle of the model is altered, placing the model in genu valgum or "knock knee," it is possible to for the final brace to be arranged to generate a medially directed force on the knee joint. In this example, the shape of the brace frame during articulation of the hinges would offload a load on the medial compartment while also creating a load in the lateral compartment. A correction offered may be limited to +/−3° from the users existing anatomical alignment. It is possible to also provide offloading of the lateral compartment/loading of the medial compartment by building the brace in relative genu varum (or bow-leggedness) as compared to the user.

After a PCL injury, the deficient or even post reconstruction ligament allows the tibia to sag posteriorly relative to the femur. The adjustment system, as in preceding embodiments of the dynamic brace, generates controlled and increasing posterior calf loads relative to the flexion angle. This load attempts to manipulate in a controlled way, the sagittal plane tibiofemoral alignment with the intension of reducing tension on the PCL ligament. As it heals, the ligament is prevented from stretching/elongation.

Post PCL injury, patients often report increased patellofemoral pain. This is presumably due to altered alignment/abhorrent joint surface contact due to the sag. Through application of aforementioned embodiments, it is believed that the alteration in tibiofemoral alignment can also reduce abhorrent joint surface pressures through improved anatomically correct congruence of the two bony surface. It has been show through in a study (currently unpublished; entitled "The Effect of Dynamic Bracing on Patellofemoral Compartment Pressures in PCL- and PCL/PLC-Deficient Knees") there is a reduction of peak joint pressures by 30%.

In the study to determine the effect of dynamic bracing on patellofemeroal compartment pressures in a PCL and PCL/PLC (posterolateral corner) deficient knee, the aforementioned embodiments of FIGS. 15-17 of a dynamic brace, were used in combination with cadaveric knees having intact cruciate and collateral ligaments. Patellofemoral pressures were measured using a pressure mapping system via a lateral arthrotomy and the pressures were recorded at knee flexion angles of 30°, 60°, 90°, and 120° under a combined quadriceps/hamstrings load of 400N/200N. Testing was repeated in PCL- and PCL/PLC-deficient knees after application of the dynamic brace.

From the study, applying the dynamic brace, it was found that application of the dynamic brace led to significant reduction in peak patellofemoral compartment pressures in PCL deficient knees at 120° of flexion, and approached significance at 30°. It was also found that the dynamic brace led to a significant reduction in peak pressures of PCL/PLC deficient knees at 60°, 90° and 120° of flexion.

It is to be understood that not necessarily all objects or advantages may be achieved under any embodiment of the disclosure. For example, those skilled in the art will recognize that the orthopedic device may be embodied or carried out in a manner that achieves or optimizes one advantage or group of advantages as taught without achieving other objects or advantages as taught or suggested.

The skilled artisan will recognize the interchangeability of various disclosed features. Besides the variations described, other known equivalents for each feature can be mixed and matched by one of ordinary skill in this art to construct an orthopedic device under principles of the present disclosure. It will be understood by the skilled artisan that the features described may be adapted to other types of orthopedic devices. Hence this disclosure and the embodiments and variations thereof are not limited to knee braces, but can be utilized in any orthopedic devices.

Although this disclosure describes certain exemplary embodiments and examples of an orthopedic device, it therefore will be understood by those skilled in the art that the present disclosure extends beyond the specifically disclosed knee brace embodiments to other alternative embodiments and/or uses of the disclosure and obvious modifications and equivalents thereof. It is intended that the present disclosure should not be limited by the particular disclosed embodiments described above, and may be extended to orthopedic devices and supports, and other applications that may employ the features described.

The invention claimed is:

1. An orthopedic device arranged for dynamically treating a knee, the device having a central axis and a frontal plane parallel to and intersecting the central axis and dividing the device along first and second sides, the device having a medial-lateral plane dividing the device into medial and lateral sides and generally oriented perpendicular to the frontal plane, the device comprising:
   a hinge assembly;
   a frame having first and second frame components spaced apart from and connected to one another by the hinge assembly;
   a strap system extending between medial and lateral sides of the first frame component;
   at least one tensioning element having a first end secured to the strap system and a second end coupled to the hinge assembly, wherein articulation of the hinge assembly pulls the strap system toward the frontal plane by the at least one tensioning element;
   wherein the at least one tensioning element is slidably coupled to the first frame component so as to direct the strap system toward the frontal plane.

2. The orthopedic device of claim 1, wherein the strap system includes a first bracket upon which the first end of a first one of the at least one tensioning element is anchored, and a second bracket upon which a first end of a second one of the at least one tensioning element is anchored.

3. The orthopedic device of claim 2, wherein the strap system includes a strap suspended between the first and second brackets, the strap being adjustable in length between the first and second brackets thereby reducing a length defined between the first and second brackets.

4. The orthopedic device of claim 3, further comprising a shell secured to the strap between the first and second brackets, and arranged for interfacing with anatomy of the user.

5. The orthopedic device of claim 2, further comprising a shell secured to the strap system and arranged for interfacing with anatomy of the user.

6. The orthopedic device of claim 1, wherein the strap system and an anchor point of the connection of the second end of at least one tensioning element at the hinge assembly are located on a first side of the orthopedic device relative to the frontal plane.

7. The orthopedic device of claim 1, wherein the second end of the at least one tensioning element secures to a hinge plate of the hinge assembly.

8. The orthopedic device of claim 1, wherein the at least one tensioning element includes a first tensioning element securing to a first side of the strap system and coupling to a first hinge of the hinge assembly, and a second tensioning element securing to a second side of the strap system and coupling to a second hinge of the hinge assembly.

9. The orthopedic device of claim 8, wherein the first and second tensioning elements are discretely separate from one another.

10. The orthopedic device of claim 8, wherein the strap system includes a first bracket upon which the first end of the first tensioning element anchors, and a second bracket upon which a first end of the second tensioning element anchors.

11. The orthopedic device of claim 10, wherein the strap system includes a strap suspended between the first and second brackets, the strap being adjustable in length between the first and second brackets thereby reducing a length defined between the first and second brackets.

12. The orthopedic device of claim 11, further comprising a shell secured to the strap between the first and second brackets, and arranged for interfacing with anatomy of the user.

13. The orthopedic device of claim 8, wherein the first frame component includes a central cuff and first and second struts arranged on the lateral and medial sides of the orthopedic device, respectively, the first and second tensioning elements slidably coupling to the first and second struts, respectively.

14. An orthopedic device arranged for dynamically treating a knee, the device having a central axis and a frontal plane parallel to and intersecting the central axis and dividing the device along first and second sides, the device having a medial-lateral plane dividing the device into medial and lateral sides and generally oriented perpendicular to the frontal plane, the device comprising:
   a hinge assembly;
   a frame having first and second frame components spaced apart from and connected to one another by the hinge assembly;
   a strap system extending between medial and lateral sides of the first frame component;
   at least one tensioning element having a first end secured to the strap system and a second end coupled to the hinge assembly, wherein articulation of the hinge assembly pulls the strap system toward the frontal plane by the at least one tensioning element;

wherein the at least one tensioning element is arranged to extend over a portion of the first frame component proximate the hinge assembly.

15. An orthopedic device arranged for dynamically treating a knee, the device having a central axis and a frontal plane parallel to and intersecting the central axis and dividing the device along first and second sides, the device having a medial-lateral plane dividing the device into medial and lateral sides and generally oriented perpendicular to the frontal plane, the device comprising:
a hinge assembly;
a frame having first and second frame components spaced apart from and connected to one another by the hinge assembly;
a strap system extending between medial and lateral sides of the first frame component;
at least one tensioning element having a first end secured to the strap system and a second end coupled to the hinge assembly, wherein articulation of the hinge assembly pulls the strap system toward the frontal plane by the at least one tensioning element;
wherein the at least one tensioning element includes a first tensioning element securing to a first side of the strap system and coupling to a first hinge of the hinge assembly, and a second tensioning element securing to a second side of the strap system and coupling to a second hinge of the hinge assembly.

16. The orthopedic device of claim 15, wherein the first and second tensioning elements are discretely separate from one another.

17. The orthopedic device of claim 15, wherein the strap system includes a first bracket upon which the first end of the first tensioning element anchors, and a second bracket upon which a first end of the second tensioning element anchors.

18. The orthopedic device of claim 17, wherein the strap system includes a strap suspended between the first and second brackets, the strap being adjustable in length between the first and second brackets thereby reducing a length defined between the first and second brackets.

19. The orthopedic device of claim 18, further comprising a shell secured to the strap between the first and second brackets, and arranged for interfacing with anatomy of the user.

20. The orthopedic device of claim 15, wherein the first frame component includes a central cuff and first and second struts arranged on the lateral and medial sides of the orthopedic device, respectively, the first and second tensioning elements slidably coupling to the first and second struts, respectively.

* * * * *